US007862652B2

(12) United States Patent
Deymier et al.

(10) Patent No.: US 7,862,652 B2
(45) Date of Patent: Jan. 4, 2011

(54) DIRECTIONAL SELF-ASSEMBLY OF BIOLOGICAL ELECTRICAL INTERCONNECTS

(75) Inventors: Pierre Deymier, Tucson, AZ (US); Ian Jongewaard, Tucson, AZ (US); Almoi Nyls Jongewaard, legal representative, Castro Valley, CA (US); James B. Hoying, Tucson, AZ (US); Roberto Guzman, Tucson, AZ (US); Srini Raghavan, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 655 days.

(21) Appl. No.: 11/418,817

(22) Filed: May 4, 2006

(65) Prior Publication Data

US 2007/0059727 A1 Mar. 15, 2007

Related U.S. Application Data

(60) Provisional application No. 60/677,734, filed on May 4, 2005.

(51) Int. Cl.

| | |
|---|---|
| ***C23C 16/00*** | (2006.01) |
| ***C23C 18/00*** | (2006.01) |
| ***C23C 18/44*** | (2006.01) |
| ***C23C 20/00*** | (2006.01) |

(52) U.S. Cl. .................................................... 106/1.05

(58) Field of Classification Search ....................... None
See application file for complete search history.

(56) References Cited

U.S. PATENT DOCUMENTS

| | | | | |
|---|---|---|---|---|
| 6,824,794 | B2 * | 11/2004 | Ring et al. | 424/638 |
| 7,205,096 | B2 * | 4/2007 | Park et al. | 430/311 |
| 2004/0063915 | A1 * | 4/2004 | Diner et al. | 530/391.1 |

FOREIGN PATENT DOCUMENTS

WO WO 2006/119472 11/2006

OTHER PUBLICATIONS

Arnal, et al. (1995) Current Biology, 5: 900-908.*

Kim, et al. (1998) Protein Science, 7: 1930-38.*

International Preliminary Report on Patentability, Corresponding to International Patent Application No. PCT/US2006/017299, Mailed Mar. 26, 2009.

Antikainen et al. (2005) "Altering Protein Specificity: Techniques and Applications," *Bioorganic Med. Chem.* 13(8):2701-2716.

Behrens et al. (Nov. 2002) "Nanoscale Particle Arrays Induced by Highly Ordered Protein Assemblies," Adv. Mater. 14(22):1621-1625.

Boal et al. (Jan. 2004) Microtubule-Templated Biomimetic Mineralization of Lepidocrocite, Adv. Funct. Mater. 14:19-24.

Bornens et al. (2002) "Centrosome Composition and Microtubule Anchoring Mechanisms," Curr. Opin. Cell. Biol. 14:25-34.

Deymier et al. (Aug. 2005) "Effect of Tubulin Diffusion on Polymerization of Microtubules," Phys. Rev. E 72:021906.

Fritzsche et al. (1999) "Wiring of metalized microtubules by electron beam-induced structuring," Nanotechnology 10:331-335.

Heald et al. (1996) "Self-Organization of Microtubules into Bipolar Spindles Around Artificial Chromosomes in Xenopus Egg Extracts," Nature 382:420-425.

Job et al. (2003) "Microtubule Nucleation," Curr. Opin. Cell Biol. 15(1):111-117.

Kinoshita et al. (2001) "Reconstitution of Physiological Microtubule Dynamics Using Purified Components," Science 294:1340-1343.

Kinoshita et al. (Jun. 2002) "XMAP215: A Key Component of the Dynamic Microtubule Cytoskeleton," Trends Cell. Biol. 12:267-273.

Kirsch et al. (1997) "Three-Dimensional Metallization of Microtubules," Thin Solid Films 305:248-253.

Limberis et al. (2001) "Polarized Alignment and Surface Immobilization of Microtubules for Kinesin-Powered Nanodevices," Nano Lett. 1(5):277-280.

Matsui et al. (2000) "Bolaamphiphile Nanotube-Templated Metallized Wires," J. Phys. Chem. B 104:9576-9579.

Mertig et al. (1998) "Biomolecular Approach to Nanotube Fabrication," Applied Physics A 66:S723-S727.

Mitchison et al. (1984) "Dynamic Instability of Microtubule Growth," Nature 312:237-242.

Sarikaya et al. (2003) "Molecular Biomimetics: Nanotechnology Through Biology," *Nature Materials* 2(9):577-585.

Schuyler et al. (2001) "Microtubule 'Plus-End-Tracking Proteins': The End is Just the Beginning," Cell 105(4):421-424.

Shacham-Diamand, Y. (1991) "100 nm wide copper lines made by selective electroless deposition," J. Micromech. Microengr. 1:66-72.

Simon et al. (1990) "The Structure of Microtubule Ends During the Elongation and Shortening Phases of Dynamic Instability Examined by Negative-Stain Electron Microscopy," *J. Cell Sci.* 96(4):571-582.

(Continued)

*Primary Examiner*—Robert M Kelly
(74) *Attorney, Agent, or Firm*—Greelee Sullivan P.C.

(57) ABSTRACT

Microtubules are excellent candidates for the fabrication of nanostructures, including nanowires. A method for controlled nucleation and growth of microtubules on substrates (e.g., gold on a silicon wafer) is provided. The substrate is functionalized with a nucleating agent for microtubule growth. The method can be employed to generate nanoscale structures on substrates or between substrates by additional attachment of MT capture agents which function to capture the ends of growing MT to form connecting MT structures. The method can be used to form 2- and 3-D structures on or between substrates and can function to establish interconnects between nanoscale devices or molecular electronic devices and electrodes. A specific method for metallization of biological macromolecules and structures in provides which can be beneficially applied to metallized the MT formed by the growth and capture method. The metallization method is biologically benign and is particularly useful for copper metallization of MTs.

27 Claims, 5 Drawing Sheets

OTHER PUBLICATIONS

Trzaskowski et al. (2006) "Metallization of Nanobiostructures: A Theoretical Study of Copper Nanowires Growth in Microtubules," J. Mater. Chem. 16:4649-4656.

Whaley et al. (2000) "Selection of Peptides with Semiconductor Binding Specificity for Directed Nanocrystal Assembly," *Nature* 405:665-668.

Yang et al. (2006) "Nucleation and Growth of Microtubules from γ-Tubulin-Functionalized Gold Surfaces," Biotechnol. Prog. 22:303-312 (Web Release Date; Jun. 7, 2006).

Yang et al. (2004) "Electroless Metal Plating of Microtubules: Effect of Microtubule-Associated Proteins," J. Mater. Sci. 39:1927-1933.

* cited by examiner

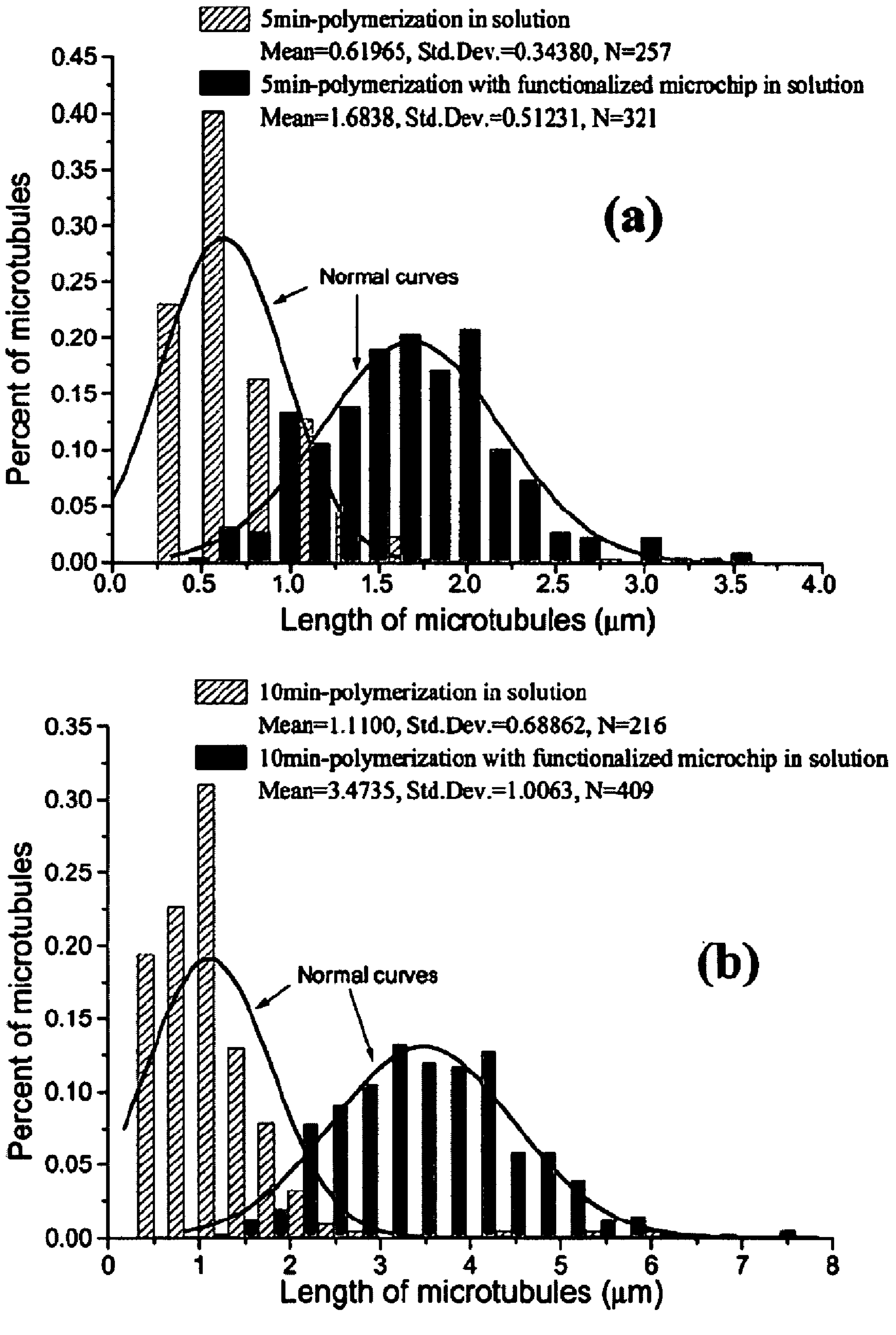
Figs. 3A-B

DIRECTIONAL SELF-ASSEMBLY OF BIOLOGICAL ELECTRICAL INTERCONNECTS

CROSS REFERENCE TO RELATED APPLICATIONS

This application claims the benefit of U.S. provisional patent application Ser. No. 60/677,734, filed May 4, 2005, the entire contents of which are incorporated by reference herein.

STATEMENT REGARDING U.S. GOVERNMENT FUNDING

This invention was funded by the United States Government under National Science Foundation contract No. 0303863. The U.S. government has certain rights in this invention

BACKGROUND OF THE INVENTION

In the semiconductor industry there has been an ongoing trend towards smaller and smaller electronic circuits and devices. This technology has been sustained by modifying the capabilities of manufacturing processes such as photolithography. Such top-bottom manufacturing methods are reaching their limits in attempts to develop smaller feature sizes. Implementation of a bottom-up method is now sought after for the manufacture of nanoscale electronic circuits. A bottom-up method utilizes the self-assembly nature of biological structures for the formation of structures from atomic or molecular constituents. Control of interconnections emerges as one of the major challenges in the development of these bottom-up approaches. Research suggests that proteins and assemblies of proteins offer the control necessary for inexpensive and reliable fabrication of nanoscale interconnects. One approach to the fabrication of interconnects for semiconductor application has involved using biological molecules as templates for metallization.

Microtubules (MT) are naturally formed tubular structures, 25 nm in outer diameter with inner diameter of 15 nm and lengths of several micrometers (Schuyler, S. C.; Pellman, D. Microtubule 'plus-end-tracking proteins': the end is just the beginning. *Cell* 2001, 105(4), 421-424). MTs are biopolymers assembled from protein heterodimers containing both alpha- and beta-tubulin (see FIG. 1). In the presence of the small molecule guanosine triphosphate (GTP), the tubulin heterodimer (Tu-GTP) self-assembles into the MT structure. The MTs' aspect ratio, chemical polarity, reversibility in assembly and ability to be metalized by electroless plating (2-3) make them good candidates to serve as templates for the fabrication of nanoscale systems, including those based on metallic nanowires (Mertig, M.; Kirsch, R.; Pompe, W. Biomolecular approach to nanotube fabrication. *Applied Physics A*. 1998, 66, S723-S727). In addition, microtubules can provide biological interactions with a native high specificity (Whaley, S. R.; English, D. S.; Hu, E. L.; Barbara, P. F. & Belcher, A. M. Selection of peptides with semiconductor binding specificity for directed nanocrystal assembly. *Nature* 2000, 405, 665-668; Sarikaya, M.; Tamerler, C.; Jen, A. K. Molecular biomimetics: nanotechnology through biology. *Nature Materials* 2003, 2(9), 577-585; Antikainen, N. M.; Martin, S. F. Altering protein specificity: techniques and applications. *Bioorganic & Medicinal Chemistry* 2005, 13(8), 2701-2716). The exposure of different tubulin regions at either end of a microtubule (the plus or minus ends) makes it possible to control MT attachment to substrates in a specific orientation.

For example, Limberis et al. took advantage of the polarity and specificity of biological interactions of MTs to flow-align pre-grown MTs immobilized onto a silica substrate using a single-chain antibody that binds only to a portion of α-tubulin exposed at the MT minus end (Limberis, L.; Magda, J. J.; Stewart, R. J. Polarized Alignment and Surface Immobilization of Microtubules for Kinesin-Powered Nanodevices. *Nano Lett.* 2001, 1(5), 277-280).

MTs are polarized with a slow-growing end (the so-called minus end exposing α-tubulin) and fast-growing end (the β-tubulin terminated plus end). The plus end of a MT typically grows at a rate 5 to 10 times faster than the minus end. In vitro, MTs can be grown from solutions containing high concentrations of purified tubulin (Johnson, K. A.; Borisy, G. G. Kinetic analysis of microtubule self-assembly in vitro. *J Mol. Biol.* 1977, 117, 1-31; Bayley, P. M.; Martin, S. R. Inhibition of microtubule elongation by GDP. *Biochemical and Biophysical Research Communications* 1986, 137(1), 351-358; M. Caplow, J. Shanks, S. Breidenbach, R. L. Ruhlen, Kinetics and mechanism of microtubule length changes by dynamic instability. *J. Biol. Chem.* 1988, 263(22), 10943-10951; Simon, J. R.; Salmon, E. D. The structure of microtubule ends during the elongation and shortening phases of dynamic instability examined by negative-stain electron microscopy. *J. Cell Sci.* 1990, 96(4), 571-582; Kowalski, R. J.; Williams, R. C. Jr. Microtubule-associated protein 2 alters the dynamic properties of microtubule assembly and disassembly. *J. Biol. Chem.* 1993, 268(13), 9847-9855; Marx, A.; Mandelkow, E. A model of microtubule oscillations. *European Biophysics Journal* 1994, 22(6), 405-421; Caudron, N.; Valiron, O.; Usson, Y.; Valiron, P.; Job, D. A reassessment of the factors affecting microtubule assembly and disassembly in vitro. *Journal of Molecular Biology* 2000, 297(1), 211-220). Microtubules generated from pure tubulin exist in a dynamic state (called dynamic instability) with net addition of tubulin to the plus end and net removal of tubulin from the minus end. This "treadmilling" effect can be controlled via interaction of the MT with various chemical agents (i.e. microtubule associated proteins (MAP), taxol) resulting in relatively stable MTs (Kinoshita, K.; Arnal, I.; Desai, A.; Drechsel, D. N.; Hyman, A. A. Reconstitution of physiological microtubule dynamics using purified components. *Science* 2001, 294, 1340-1343; Arnal, I.; Wade, R. H. How does taxol stabilize microtubules? *Current Biology* 1995, 5, 900-908).

In the absence of these agents and for tubulin concentrations below a critical value, $C_c$, MTs will depolymerize (Lodish, H.; Berk, A.; Zipuski, S. L.; Matsudaira, P.; Baltimore, D. and Darnell, J. "Molecular Cell Biology," $4^{th}$ Edition, Freeman, 2000.) Tubulin dimers polymerize into MTs for tubulin concentrations above $C_c$. At concentrations of tubulin dimers near $C_c$, individual MTs exhibit dynamic instability (Mitchison, T. and Kirschner, M. Microtubule assembly nucleated by isolated centrosomes. *Nature* 1984, 312, 237-242.) and undergo apparently random successive periods of disassembly (catastrophe) and assembly (rescue). The mechanism for transition between a growing state and a shrinking state is generally believed to be associated with hydrolysis of bound GTP when tubulin heterodimers become incorporated within the microtubule structure. While the process of MT growth is reasonably well understood, in vivo and in vitro MT nucleation is, however, still poorly understood. Within the cell, the minus end is tethered to microtubule-organizing centers (MTOC) such as centrosomes, and the plus end extends into the cytoplasm (Job, D.; Valiron, O.; Oakley, B. *Microtubule nucleation. Current Opinion in Cell Biology* 2003, 15(1), 111-117). MT assembly is believed to nucleate from the MTOC through interaction with a tubulin isoform, gamma-tubulin (Moritz, M.; Zheng, Y.; Alberts, B. M.; Oegema, K. Recruitment of the gamma-Tubulin Ring Complex to *Drosophila* Salt-stripped Centrosome Scaffolds. *J Cell Biol.* 1998, 142, 775-786; Schnackenberg, B. J.; Khodjakov, A.; Rieder, C. L.; Palazzo, R. E. The disassembly and reassembly of functional centrosomes in vitro. *Proc Natl Acad Sci USA* 1998, 95, 9295-3900; Gunawardane, R. N.; Lizarraga, S. B.; Wiese, C.; Wilde, A.; Zheng, Y. Gamma-Tubulin complexes and their role in microtubule nucleation. *Curr. Top Dev. Biol.* 2000, 49, 55-73). Research in vitro has shown that gamma-tubulin is an essential component in the centrosome for microtubule nucleation (Felix, M. A.; Antony, C.; Wright, M.; Maro, B. Centrosome assembly in vitro: role of gamma-tubulin recruitment in *Xenopus* sperm aster formation. *J. Cell Biol.* 1994, 124, 19-31; Stearns, T.; Kirschner, M. In vitro reconstitution of centrosome assembly and function: the central role of gamma-tubulin. *Cell* 1994, 76, 623-637).

Monomeric gamma-tubulin and gamma-tubulin protein complexes can both nucleate MT. The nucleation time of MTs has been shown to be shorter in the presence of monomeric gamma-tubulin (Leguy, R.; Melki, R.; Pantaloni, D.; Carlier, M. F. Monomeric gamma-tubulin nucleates microtubules. *J. Bio. Chem.* 2000, 275(29), 21975-21980). In vitro, monomeric gamma-tubulin behaves as a minus-end-specific protein, with very high binding specificity to the microtubule end. It caps microtubule minus ends and catalyzes microtubule nucleation (Leguy, R.; Melki, R.; Pantaloni, D.; Carlier, M. F. Monomeric gamma-tubulin nucleates microtubules. *J. Bio. Chem.* 2000, 275(29), 21975-21980; Li, Q.; Joshi, H. C.; Gamma-tubulin is a minus end-specific microtubule binding protein. *J. Cell Biol.* 1995, 131, 207-214). Specific peptides and/or complexes of gamma-tubulin have also been identified to serve as binding sites to interact with tubulin heterodimers (Llanos, R.; Chevrier, V.; Ronjat, M.; Meurer-Grob, P.; Martinez, P.; Frank, R.; Bornens, M.; Wade, R. H.; Wehland, J.; Job, D. Tubulin binding sites on gamma-tubulin: identification and molecular characterization. *Biochemistry* 1999, 38, 15712-15720; Fuller, S. D.; Gowen, B. E.; Reinsch, S.; Sawyer, A.; Buendia, B.; Wepf, R.; Karsenti, E. The core of the mammalian centriole contains gamma-tubulin. *Curr Biol.* 1995, 5(12), 1384-1393; Moritz, M.; Braunfeld, M. B.; Sedat, J. W.; Alberts, B.; Agard, D. A. Microtubule nucleation by g-tubulin-containing rings in the centrosome. *Nature* (*London*), 1995, 378(6557), 638-640; Wiese, C.; Zheng, Y. A new function for the g-tubulin complex as a microtubule minus-end cap. *Nature Cell Biology* 2000, 3, 358-364; Oegema, K.; Wiese, C.; Martin, O. C.; Milligan, R. A.; Iwamatsu, A.; Mitchison, T. J.; Zheng, Y. Characterization of two related *Drosophila* gamma-tubulin complexes that differ in their ability to nucleate microtubules. *J. Cell Biol.* 1999, 144, 721-733). Gamma-tubulin ring complex (gamma-TuRC), which also binds to the minus ends of microtubules, can also work as a nucleation center for growth of the microtubule both in vivo and in vitro (Fuller, S. D.; Gowen, B. E.; Reinsch, S.; Sawyer, A.; Buendia, B.; Wepf, R.; Karsenti, E. The core of the mammalian centriole contains gamma-tubulin. *Curr Biol.* 1995, 5(12), 1384-1393; Moritz, M.; Braunfeld, M. B.; Sedat, J. W.; Alberts, B.; Agard, D. A. Microtubule nucleation by g-tubulin-containing rings in the centrosome. *Nature* (*London*), 1995, 378(6557), 638-640; Wiese, C.; Zheng, Y. A new function for the g-tubulin complex as a microtubule minus-end cap. *Nature Cell Biology* 2000, 3, 358-364). In addition to gamma-TuRC, several smaller gamma-tubulin complexes, called gamma-tubulin small complexes (gamma-TuSCs) are identified as components of gamma-TuRC(32). Gamma-TuSCs can also nucleate microtubule in tubulin solutions but with lower efficiency compared with gamma-TuRCs(32). Besides growing from centrosomal sites, MTs also can grow from noncentrosomal sites in the cell. In the absence of a centrosome, other mechanisms must operate to organize free MTs. One such mechanism is self-organization, which can produce MT asters, bundles, and bipolar spindles. It has been shown that microtubules can also grow from some small chromatin-coated beads (Heald, R.; Tournebize, R.; Blank, T.; Sandaltzopoulos, R.; Becker, P.; Hyman, A.; Karsenti, E. Self-organization of microtubules into bipolar spindles around artificial chromosomes in *Xenopus* egg extracts. Nature 1996, 382, 420-425).

This invention relates to the use of microtubules (MT) to form 2D- and 3D-structures on, between and among substrates. Creation of such structures relies on in-situ growth of MTs from selected nucleation sites on substrates and the capture of growing ends (+ends) of the MTs at selected capture sites separated from the nucleation sites. These structures can be generally used as nanoscale templates, as scaffolds for attachment and location of nanoscale objects. More specifically the can be used as templates for fabricating nanoscale interconnects, interconnect arrays, and networks. The ability to create and use arrays or structures of MTs, particularly as templates for interconnecting devices on microchips, necessitates the development of a protocol where MTs can be nucleated and directionally grown from specific sites on the microchip toward some target capture site elsewhere on that chip. As a step in the process of manufacturing MT-based nanostructures on a silicon wafer, this invention provides an "in situ" approach to forming MT-based nanostructures comprising functionalizing selected different sites on a substrate (e.g., a metal pad) with derivatized MT nucleating complexes and derivatized MT capture complexes, followed by surface-driven growth of MTs from nucleating sites followed by capture of growing MTs at capture sites to form an MT structural link between two selected sites on a substrate. The advantage of this approach lies not only in the immobilization of MTs on the surface of a substrate, but more importantly on the unique ability to initiate MT growth from selected sites and the ability to generate MT's between selected sites.

Another requirement in the manufacture of MT-based nanostructures for forming electrical circuits and devices is the development of improved metallization techniques. Several biological templates have already been shown to form nanostructures through metallization processes. In a study by Braun et al., DNA is used as a template for creating a 12 μm long and 100 nm wide silver wire. This was accomplished by first fixing the DNA between gold electrodes followed by selective localization of silver ions along the DNA skeleton; the silver-ions were then reduced to silver metal aggregates along the DNA to yield a nanowire which exhibited granular morphology and the ability to conduct electrical current [E. Braun, Y. Eichen, U. Sivan, G. Ben-Yoseph, Nature 1998, 391, 775.]. Similarly, DNA has also been metalized with nanoscale palladium clusters. The DNA was activated with Pd ions and then added to a reduction bath containing dimethylamine borane (DMAB) as the reducing agent. Over time the initial clusters that formed on the surface become a continuous metallic surface [J. Richter et al, Adv. Mater. 2000, 12(7), 507].

Others have used viruses, which are essentially helical RNA, as the substrate for the plating of nickel and cobalt metal. A tubular virus, tobacco mosaic virus, was metalized on the inner and outer surfaces. This selective metallization was regulated by the absence or presence of phosphate that interacted with functional groups that differed on the inside and outside surfaces [M. Knez et al, Nano Letters 2003, 3(8), 1079 and M. Knez et al, Adv. Funct. Mater. 2004, 14(2), 116].

Microtubules have also been coated by electroless deposition of nickel and cobalt. Electroless deposition is a redox reaction, in which a cation of a metal is chemically reduced onto a surface to form a metal film. Typically, the metallization of MTs involves a two step process of activating the MT surface with a noble metal such as Pd or Pt, which is a catalyst for the electroless deposition of the desired metal. Nickel plating of MTs was carried out under physiological conditions, between 30-60° C. and between pH 6 and 8. The metallization process produced nickel only in areas where the Pd catalysts were deposited. While Pd and Pt ions have the capability to diffuse through the MT wall, no deposition was observed on the inner channel due to the rapid metal deposition on the outer surface which blocked ion penetration. Nickel nanowires generated had an overall diameter of 50 to 60 nm. Similar results were reported for cobalt metallization [R. Kirsch, M. Mertig, W. Pompe, R. Wahl, G. Sadowski, K. J. Böhm, and E. Unger, Thin Solid Films 1997, 305, 248; M. Mertig, R. Kirsch, W. Pompe, Applied Physics A 1998, 66, S723.]. MTs have also been metalized with Pd which was proposed to proceed by binding of Pd particles with histidine amino acids on the surface. The surface of the MTs was covered with palladium particles of 2 to 3 nm to form quasi-continuous coverage up to 100 nm in diameter [S. Behrens, K. Rahn, W. Habicht, K. J. Böhm, H. Rösner, E. Dinjus, E. Unger Adv. Mater. 2002, 14(22), 1621].

U.S. published patent application 20040063915 relates to metallization of MTs by reacting “fixed” microtubules with a reducible metal salt. MTs are fixed by treatment with glutaraldehyde. Noble metal salts, e.g., $HAuCl_4$, in combination with a reducing agent ($NaBH_4$ or sodium ascorbate) are used to metalize fixed MTs. Additional salts are said to be useful in the method, including $AgNO_3$, $HPtCl_3$, $CuNO_3$, and $K_2PdCl_4$.

Copper metallization of templates to produce nanostructures is of particular interest to the semiconductor industry, because copper is currently the interconnect metal of choice in integrated circuits. Copper is a more desired metal than nickel or cobalt due to its lower resistivity. U.S. published patent application 20040063915 suggests that MTs can be metalized employing $CuNO_3$ as a reducible salt, but does not demonstrate copper metallization of MTS. Furthermore, the published application requires fixing of MTs prior to metallization. Copper plating on bolaamphiphile nanotubes [H. Matsui, S. Pan, B. Gologan, and S. H. Jonas, J. Phys. Chem. B 2000, 104, 9576] has been reported. Bolaamphiphiles are self-assembling, organic structures in the form of a crystalline tubule with an average diameter of 700 nm and a length of 10 μm. Metallization with copper and nickel was carried out by exposure to an electroless nickel or copper bath with the reducing agents hypophosphite and dimethylamineborane (DMAB), respectively. The copper coated nanotubes had a diameter of 700 nm and the nickel coated tubes had a diameter of 1 μm. Metallization occurred with and without the initial activation of the surface with a Pd catalyst. The metallization was reported to result from the binding of ions to available amine groups in the peptide followed by reduction of these ions to metal in the plating baths.

Electroless deposition of copper onto the MT surface poses a challenge, because the commercially available plating baths contain formaldehyde which damage or destroy MTs. Conditions typically employed for electroless deposition of copper are very harsh—alkaline pH values (11.5 to 13) and temperatures from 55° C. to 70° C. which are detrimental to MTs [Y. Shacham-Diamand, J. Micromech. Microengr., 1991, 1, 66].

The present invention provides an improved method for metallization of MTs and other biological templates by electroless deposition of copper and other metals onto MTs. The method employs reducible salts, such as $CuSO_4$, in the presence of a reducing agent at pH of 4 or less which is not detrimental to MT function and structure. Furthermore, the metallization method is compatible with the methods herein for growth of MTs structures on substrates. Additionally, the method has been found to be useful for forming metalized MTs having diameters of 15 nm or more. In order to obtain metalized MTs of such small diameters, it is believed that metallization of MTs with Cu at least proceeds through deposition of metal inside of the MTs.

SUMMARY OF THE INVENTION

The invention provides methods for generating nanoscale structures comprising microtubules on, between or among one or more substrates. The method involves the nucleation of MTs from selected sites on a substrate and the capture of growing MTs to form an interconnect between the nucleation site and the capture site. Nucleation sites are typically established on a substrate by attachment of one or more MT nucleation complexes. Nucleation sites may be established however on nanoscale devices (e.g., quantum dots or the like) or at molecular electronic devices (e.g., photovoltaic molecules or polymer diodes or transistors). MT capture sites can likewise be established on a substrate or device to which an attachment can be made by attachment of MT capture complexes.

More specifically, one or more MT nucleating complexes are attached on one or more substrates at one or more selected nucleation sites on the substrates. MT growth is initiated by contacting the immobilized MT nucleation complex with an MT growth composition comprising GTP, alpha and beta tubulin and a MT stabilizing agent. One or more MT capture complexes are attached to one or more substrates at one or more sites or to a nanoscale or molecular device. Nucleation sites and/or capture sites can be established at one or more distinct locations on a substrate. Growing MTs that encounter a capture site can be captured by the site to form an interconnect between the nucleation site and the capture site. After capture, MT which may have initiated and grown, but which have not been captured can be depolymerized and removed. This operation of attachment, growth initiation, capture and removal results in the formation of an nanoscale structure on, between or among substrates or nanoscale or molecular devices, MT growth is continued until at least one MT interconnect is formed and more preferably is continued until a desired 2 or 3-D nanoscale structure is formed. Non-captured MT and residual MT growth composition can simply be removed by washing or dilution.

MT growth is carried out under conditions that are permissive for that growth. Temperature, pH and concentration of required MT growth components can be adjusted based on the teachings herein and what is known in the art to achieve desired MT growth.

After initial attachment steps, the growth, capture and removal steps of the method can be repeated a plurality of times to achieve a desired structure. Alternatively the attachment, growth, capture and removal steps can be repeated a plurality of times to achieve a desired structure. The method can be practiced such that the direction of growth of the MT from at least a portion of the nucleation sites is controlled. The direction of MT growth can be controlled in a variety of ways, e.g., by establishing a directional fluid flow, by application of electric fields, or by establishing concentration gradients of required growth components such ad GTP. The method can be practiced by varying the direction of MT growth to achieve a desired structure. The growth, capture and removal steps can be repeated a plurality of times with different growth directions imposed. The attachment, growth, capture and removal steps can be repeated a plurality of times with different growth directions imposed In specific embodiments the MT nucleating complex comprises gamma-tubulin, particularly a gamma tubulin that is tagged for selective attachment to a substrate or device. A variety of different tagging, labeling and attachment methods can be employed to achieve selective attachment to sites on a substrate or to different devices. GST-tagged and His-tagged gamma-tubulin can be used as MT nucleating complexes, for example.

In specific embodiments MT capture complex comprises alpha-tubulin. In other embodiments the MT capture complex comprises CLIP 170. The capture proteins are tagged for selective attachment to a substrate or device. A variety of different tagging, labeling and attachment methods can be employed to achieve selective attachment to sites on a substrate or to different devices. GST-tagged and His-tagged alpha-tubulin and/or GST-tagged and His-tagged CLIP 170 can be used as MT capture complexes, for example.

MT structures formed by the methods herein are immobilized on, between or among substrates. The MT structures can form interconnects or interconnect arrays between and among one or more than one substrate or device.

MT structures formed by the method herein can be fixed or crosslinked to further stabilize the MT structure. MT structures are preferably metallized to provide electrically conductive interconnects. Any art-known method of metallization that has been successfully applied to metallization of biological templates can be employed. Metallization may be preceded by a fixation or crosslinking step as is known in the art. Alternatively, a biologically benign metallization, such as that described in another aspect of this invention can be employed. The metallization method of this invention is particularly useful for metallization of the inner surface of MTs to form narrow diameter nanowires. The metallization method of this invention can be employed, for example, to metallize the MT structures herein with copper.

The invention also provides kits for preparation of nanoscale structures on or between substrates which comprises in individual packing units (vials and the like) a plurality of MT nucleating complexes which are selectively tagged with different tags for selective attachment to a substrate, a plurality of MT capture complexes which are selectively tagged with different tags for selective attachment to a substrate wherein MT nucleating complexes having different tags and MT capture complexes having different tags are individually packaged for use. These kits may comprises MT nucleating complex subsets which are differentially tagged gamma-tubulins and MT capture complex subsets which are differentially tagged alpha-tubulins and/or subsets of differentially tagged CLIP 170 proteins. Kits are useful for the convenient practice of the invention and kits may also comprises one or more of the following components: instructions for carrying out the method, MT growth components (individually packaged), buffers or washing solutions, one or more substrates, one or more nanoscale devices (e.g., quantum dots), or metallization solution components.

In another aspect, the invention relates to a method for metallization of biological macromolecules and biological structures, particularly those which self-assemble. The method is an electroless metal deposition. The method is biologically-compatible in that it achieves metallization under conditions (temperature and pH) in which the biological macromolecule or structure substantially retains its structure without the need for prior treatment with a fixative or cross-linking agent. The method is particularly useful for metallization of biological macromolecules with copper. The method is particularly useful for metallization of protein-containing structures, particularly protein structures containing a plurality of protein subunits. In specific embodiments, the method is applicable to protein-containing structures including, but not limited to, self-assembling subcellular structures such as microtubules and actin filaments, intermediate filaments, collagen fibers, fibrin, alpha-helical polypeptides, flagella, cilia, pili, fibrils, as well as viruses (e.g., tobacco mosaic virus (TMV) or parts thereof (e.g., viral tail fibers).

Metallization may be conducted to provide a continuous metal coating over an entire surface or the metal coating may be discontinuous. In preferred embodiments the metal coating is continuous. In preferred embodiments, the metal coating is of uniform thickness. The method is optionally employed to deposit a mixture of two or more metals onto the biologically macromolecule or structure. In specific embodiments, the biological macromolecule or structure is covalently or non-covalently attached to a substrate. In specific embodiments, the biological macromolecule or structure is a microtubule.

More specifically, the method involves contacting the biological macromolecule or structure with a reducible metal salt or complex, e.g., a copper salt, in the presence of a reducing agent. Metal sulfates, nitrates, halides (e.g., chlorides) and metal acetate complexes are useful in this method. The reducing agent functions to reduce metal ions which plate out or are deposited on a surface of the biological macromolecule or structure. The surface that is coated or plated with metal may be the outer surface of the biological macromolecule or structure or, if present, the surface may be an internal or an inner surface of the biological macromolecule or structure. In specific embodiments, the method can be employed to metalize the inner surface of protein-containing hollow tubes, such as microtubules. In specific embodiment, the metallization method is employed to generate metalized microtubule nanowires. In specific embodiments, the metalized microtubule nanowires have diameters of about 15 nanometers or more. In specific embodiments, the metalized microtubule nanowires are metalized with copper. Nanowires made by the methods herein are useful for forming nanoscale electrical interconnects.

In specific embodiments, metalization is conducted in the presence of a stabilizing agent which stabilizes the structure of the biological macromolecule or structure. In specific embodiments, microtubules are metalized in the presence of taxol or a MAP (Microtubule Associated Protein).

In specific embodiments, the metallization employs a copper (II) salt or complex in the presence of a reducing agent, such as ascorbate. In specific embodiments, Cu-metallization is initiated at one or more histidine residues on a surface of the biological macromolecule. In specific embodiments, Cu-metallization is initiated on one or more protein surfaces comprising one or more histidines that are available for complexation to copper ions. In specific embodiments, the metallization is conducted by contacting the biological macromolecule or structure with the metallization components in aqueous solution at a pH and temperature at which the biological macromolecule or structure is substantially stable (i.e., is sufficiently stable to allow the macromolecule or structure to be metalized before it disassembles or is otherwise damaged). In specific embodiments, the metallization components are a copper (II) salt, a reducing agent, preferably ascorbic acid or ascorbate, and a complexant, such as acetic acid (acetate) or other carboxylic acid (carboxylate).

In a specific embodiment, the method involves contacting microtubules with a reducible metal salt or metal complex in the presence of a reducing agent and optionally in the presence of a complexant.

BRIEF DESCRIPTION OF THE DRAWINGS

FIGS. 3A and B are graphs illustrating the length distribution of MT polymerized for min (A) and 10 min (B) in solution as described in Example 3 and from a square array of gamma-tubulin-functionalized gold pads.

DETAILED DESCRIPTION OF THE INVENTION

Figure 1:
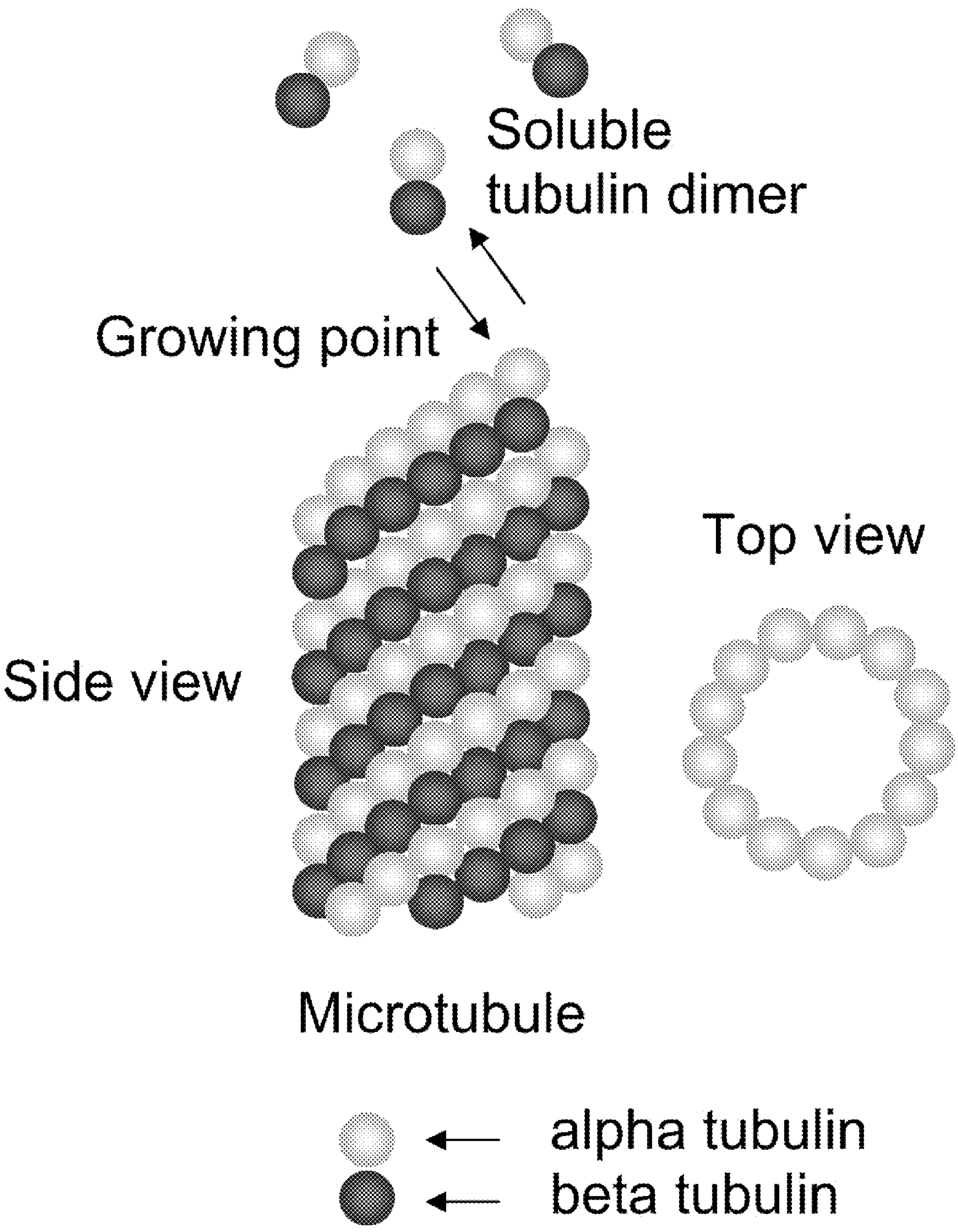
FIG. 1 is a schematic illustration of the structure of a microtubule (MT) indicating the alpha-tubulin/beta-tubulin heterodimer components of the tubule. The microtubule is a hollow tube (see top view) with a tubular interior cavity defined by an inner or interior wall. The growing end is labeled

The method of this invention for growth and subsequent capture of MTs can be employed to create interconnects between or among defined locations on a single substrate or between or among two or more substrates, between a substrate and a nanoscale device or an molecular electronic device (e.g., a molecule which exhibit desirable electronic properties, such as a photovoltaic molecule), between or among nanoscale devices or molecular electronic device optionally attached to a substrate, between or among electrodes on one or more substrates, and between one or more electrodes on one or more substrates and one or more nanoscale devices or molecular electronic devices. The method can be employed to create interconnects that function as templates for metallization to provide electrically conductive interconnects. The method can be used to create 2- and 3-dimensional structures on or between one or more substrates. These structures can, for example, be used as scaffolds for attachment of molecules, including biological molecules, in a selected pattern on the structure. The structures can be used as templates in any suitable method of nanoscale manufacture, e.g., for forming nanoscale molds of the structure for replication of the structure using another material, and as masks for protecting an underlying substrate during subsequent processing, as templates for metallization. The methods can be used to create interconnect arrays and interconnect networks. In specific embodiments, the method can be used to create an interconnect between or among two or more substrates. In this case, the interconnect formed preferably is provided with or formed within a support matrix, such as a gel, to provide mechanical support for the interconnection, array, network or other structure formed. An interconnect formed between or among sites can be formed comprising a plurality of individually grown MTs.

The method of this invention can be employed to generate two connection devices such as diodes or three-connector devices such as transistors.

The method allows for parallel synthesis of a plurality of interconnects. For example, a plurality of MT can be grown from a single location wherein individual MTs are captured at a particular capture site among a plurality of different capture sites. In this case, selective attachment to different substrate locations can be achieved by used of orthogonal attachment strategies. Orthogonal attachment strategies can be accomplished, for example, by the use of selective tagging of subsets of nucleation and capture complexes with distinguishable tags and the selective attachment of ligands to distinct locations on the substrates wherein ligands attached at distinct locations have different specificities for binding to the tags on the nucleation and capture complexes.

The method can also be practiced, sequentially to form a series of different interconnects in a plurality of sequential MT growth and capture operations. Such a method would comprise, for example, a first step of selective attachment of MT nucleation complexes and capture complexes followed by growth of MTs, capture and removal of non-captured MTs, followed by a second step of selective attachment of nucleation complexes and capture complexes followed by a second MT growth, capture and removal operation. A plurality of such sequential steps can be performed.

The method of this invention can be practiced such that the direction of growth of MT from at least a portion of the nucleation sites is controlled. The method can be practiced sequentially in a plurality of MT growth and capture operations in which the direction of growth of MTs can be varied from step to step. Such a method would comprise, for example, a first step of selective attachment of MT nucleation complexes and capture complexes where growth of MT is controlled to be in a first direction with capture, followed by removal and a second growth step where growth of MT is controlled to be in a second direction with capture, followed by removal. A plurality of such sequential steps can be performed.

The method is conducted by contacting a substrate with attached nucleation and capture complexes with a liquid MT growth composition which comprises GTP, alpha and beta tubulin and a MT stabilizing agent. The liquid employed may be an aqueous solution containing suitable amounts of the listed components. The liquid employed may be a gel, such as a hydrogel, containing suitable amounts of the listed components. The use of gels or other high viscosity liquids as a carrier for MT growth can be used to provide a support matrix for growth of MTS between two or more substrates or between a substrate and one more nanoscale devices or molecular electronic devices. The gel or other high viscosity liquid can provide mechanical support for any interconnects, arrays or networks formed therein. Additional, gels or other high viscosity liquid can be used to establish concentration gradients of MT growth components, e.g., gradients of GTP, to control growth of MTs along regions of higher concentrations of GTP.

Methods of this invention employing in situ growth and capture of MTS can be combined if desired or useful with selective attachment of pre-grown MTs to substrates. Methods of this invention can be beneficially combined with art-known methods for attachment of nanoscale devices or molecular electronic devices to substrates. Methods of this invention can be combined with any suitable art-known method for creating nanoscale structures on a substrate. The methods herein can for example be employed on substrates having structured topography created by such art-known methods to create interconnects between or among distinguishable structures on a substrate, e.g., from an electrode pad formed on a substrate to a channel or raised feature on the substrate.

An MT nucleation complex is the general term used herein for a nucleation protein or complex of proteins or a microtubule initiating complex or protein is one which provides a site from which alpha-tubulin and beta-tubulin subunits can associate progressively (assemble, polymerize, elongate, more generally grow) to form a microtubule. Typically the key nucleation protein or component of the complex is gamma-tubulin or a derivative thereof, for example, a "tagged" protein, or a truncated (optionally tagged) gamma-tubulin which retains the ability to serve as a nucleation protein. Gamma-tubulins can be isolated from natural sources and purified if needed or can be synthetic. A gamma-tubulin mutant protein which differs in one or more amino acids from a wild-type gamma-tubulin, but which retains the function of MT nucleation alone or in combination with other gamma-tubulins can also be used. Alpha-tubulin or a derivative thereof, including a tagged derivative (e.g., a tagged protein), can also mediate initiation of microtubule assemble. Alpha-tubulin can be similarly modified with a tag or truncation or with amino acid changes from a wild-type alpha-tubulin, provided that its ability to serve as a nucleation site for MT growth is retained. The tag facilitates purification via affinity or immunoaffinity chromatography, and the tag can also provide the means for selective attachment of the nucleation protein or complex to a surface. Other nucleation proteins and complexes are as known to the art.

A cap (or capture) protein is one which selectively binds to the growing (plus) end of a microtubule, i.e., to β-tubulin. It can be provided free in solution and thus stabilize the formed microtubule by preventing dissociation of subunit tubulin proteins or it can be fixed to a surface, for example, via a recombinantly incorporated tag which binds a ligand which can be fixed to the surface. When the cap protein is fixed to a surface within a distance from the nucleation protein equal to or less than the length of an associated microtubule, the plus end of that microtubule can bind the immobilized cap protein and thus, the microtubule is stabilized against dissociation and it is bound at both ends to the surface from which it was assembled. Subsequent metallization of that microtubule produces an electrical connection between the nucleation and cap proteins, desirably each attached to conductive surfaces. Examples of cap proteins useful in the present invention include, but are not limited to, CLIP170 (also known as restin, sequences available on NCBI Accession Nos. NM_019765, mouse; BC114213 and BC039081, human; see also Akhmanova et al. 2005. Genes Devel. 19:2501-2515; Bilbe et al. 1992. EMBO J 11:2103-2113) and α-tubulin or a derivative thereof or an antibody, single chain antibody or Fab fragment of antibody which specifically binds β-tubulin. The cap protein can be immobilized at a discrete site on a surface in ways like those that are described for the nucleation proteins, but advantageously, the mechanism for binding the nucleation protein and the cap protein are not the same, to facilitate control of binding reactions. It is understood that there can be multiple cycles of cap and nucleation protein immobilization and microtubule polymerization, washing and additional cap and nucleation protein immobilizations (optionally following additions of electrode base materials) and polymerization so as to produce complex interconnect patterns on the solid support. As noted above for nucleation proteins, capture proteins that are modified by tagging, truncation, or amino acid changes from a wild-type capture protein, and which retain function for capture of MT can be employed in the methods herein.

A microtubule stabilizing agent is one which, when added to a microtubule assembly solution, interacts with the growing or newly produced microtubule in such a way that dissociation of that microtubule is reduced, especially in comparison to polymerization of that microtubule. Microtubule stabilizing agents can include taxol or certain other small organic molecules, or they can be proteins which interact with the microtubule, either at the plus end or along the length of the microtubule, provided that dissociation is kinetically disfavored in comparison to polymerization. XMAP215 or XKCM1 are examples of MAPs (microtubule associated proteins) which can function to enhance polymerization and/or inhibit net dissociation (see, e.g., Kinoshita et al. 2001. Science 294:1340-1343; Kinoshita et al. 2002. Trends Cell Biol. 12:267-273).

The tubulins that mediate microtubule elongation (polymerization, association or assembly) include both α- and β-tubulins. Desirably both of these are from the same biological source. However, provided that microtubules are formed the sources need not be the same. Similarly, the nucleation protein or complex and/or the cap protein or stabilizing protein can be from different biological sources (organisms) provided that interactions necessary for initiation, elongation, capping or stabilization occur. Preferably, however, these are all from mammalian sources or all from plant sources, for example.

The applicability of using MTs as templates for interconnecting devices on microchips necessitates the development of a protocol where MTs can be nucleated and directionally grown from specific sites on the microchip toward some target site elsewhere on that chip. Toward the goal of manufacturing MT-based nanostructures on a silicon wafer, we report, here an "in situ" approach consisting of a starting metal pad functionalized with a derivatized MT nucleating complex, and surface-driven growth of MTs from the pad. The advantage of this approach lies not only in the immobilization of MTs on the surface of a substrate but more importantly on the unique ability to initiate MT growth from desired sites. In addition, we also report on the effect of the geometry of the substrate on the morphology of the MTs. Based on the premise that MT growth may be influenced by the geometry of the environment, we have conducted additional experiments of MT growth from γ-tubulin functionalized surfaces with two geometrical arrangements of the substrates, namely a square lattice of small gold pads (10 μm×10 μm) on a hydrophilic oxidized silicon wafer and a large flat surface (dramatically larger as compared to the scale of MTs). Fluorescence microscopy and scanning electron microscopy are employed to provide a detailed characterization of the morphology of the nucleated and grown microtubules.

Synthesis and Purification of End-Specific Capping Proteins (a) Synthesis of a Gamma-Tubulin/Glutathione S-Transferase Fusion Protein for the Nucleation of Microtubules from Functionalized Electrodes We have created a Glutathione S-Transferase (GST)-tagged γ-Tubulin fusion protein useful as a nucleating agent for the initiation of microtubule growth. The coding sequence for GST-γ-Tubulin was created by extracting RNA from human cells, amplifying the sequence of human γ-Tubulin using Reverse Transcriptase PCR and cloning the amplification product. The sequence of the cloned amplification product was verified. The γ-Tubulin coding sequence was then cloned into a plasmid containing the sequence encoding the GST tag, which resulted in the creation of a recombinant GST-γ-Tubulin sequence, with an IPTG-inducible (lace) promoter sequence for controlled gene expression. The recombinant plasmid, which confers ampicillin resistance, was then transformed into *Escherichia coli.*

The recombinant *E. coli* cells were grown in large flasks of growth media containing Ampicillin, to select for *E. coli* containing the plasmid of interest. When the culture reached an optical density of 0.9, 1 mM Isopropyl-β-D-thiogalactopyranoside (IPTG) was added to induce the expression of the GST-γ-Tubulin protein, and the culture was incubated further to allow expression of the protein. *E. coli* cells were then collected via centrifugation and lysed using lysozyme. Cell debris was removed by centrifugation. The supernatant was loaded onto an immunoaffinity column specific for the GST tag, so that the GST-γ-Tubulin protein is bound. Unbound proteins were washed from the column, and the purified GST-γ-Tubulin protein was eluted using free glutathione. The protein quality was verified using SDS-PAGE and the eluted protein was found to be the correct size, 85 kD. The protein was also verified using ELISA, and other highly specific antibodies to GST and γ-Tubulin, which were also used to verify the protein quality (See Example 1 for additional description).

While the specifically exemplified gamma-tubulin has been expressed as a GST-fusion protein to facilitate purification, other N-terminal sequence tags are known to and readily accessible to the art. They include a Strep (Streptavidin) tag, c-Myc epitope tag, a FLAG (flagellar antigen) Epitope tag, GFP Epitope tag (green fluorescent protein), and a polyhistidine (especially popular is a hexahistidine) tag. The epitope tagged-proteins are conveniently purified using commercially available antibodies specific to the tag of interest and they can also be bound to surfaces to which the relevant antibodies have been bound. His-tagged proteins are purified using Nickel-nitrilotriacetate technology, and such proteins can be bound to appropriately modified surfaces.

A similar approach is currently used to synthesize a GST-α-Tubulin MT plus end cap for a functionalized end-target electrode.

For capture of an MT extended from a first electrode (or other discrete surface or site), there is a "cap" protein attached to a second electrode surface. The cap protein can be an α-tubulin, a CLIP170 protein, MAP protein or MT+end-specific antibody of or specific binding fragment thereof or other protein which selectively binds to the growing (+) end of the MT, with the proviso that it can be immobilized to a surface, for example with a tag sequence, desirably a tag sequence which differs from that used to immobilize the nucleation protein. Certain MAP proteins can be used, in particular, those which selectively bind to the plus end of the MT. The capture proteins are desirably made recombinantly as tagged fusion proteins after cloning the particular coding sequence as an in frame fusion in one of a number of commercially available vectors designed for tagged fusion proteins.

Specific Ligands for Various Functionalized Surfaces (a) A Library of Multifunctional Ligands We have developed a process to bind reactive alkanethiols, conjugated with different ligands, together with genetically engineered fusion proteins, to develop a protein assembling method for incorporation of MTs as bio-interconnects. Reactive Gold surfaces have been modified using Functionalized Self-Assembled Monolayers (FSAMs). FSAM of a carboxylic acid terminated alkanethiol is followed by the coupling of specific ligands for selective binding and attachment of derivative microtubule-nucleating proteins. A library of different affinity ligands allows for an immense number of combinations of specific binding schemes. This library enables multiple sites to be functionalized differently, leading to the possibility of building controlled networks of microtubule interconnections. For instance, a polypeptide with a Histidine amino acid residue binds to a surface modified with a chelating ligand, while another cap, bearing Tyrosine residues, will bind to a surface modified with thiophilic ligands. A library of ligands with alternating affinities to specific amino acid residues that form various capping-agent polypeptides is illustrated in the Table 1 below:

TABLE 1

Library of ligand linkers based upon chelating derivatives with hydrophobic, thiophilic, and covalent interactions.

| Bifunctional Reagent | Affinity Group/Interaction | Amino Acid Residue Interaction |
|---|---|---|
| Chelating ligands | Metal Ion | Peptide |
| IDA (iminodiacetate) | Cu(II) | Histidine (His) residues |
| NTA (nitrilotriacetate) | Ni(II) | Multihistidine tags |
| IDA | Pd(II) | Methionine (Met) residues, Cysteine (Cys) |
| TREN(Tris(2aminoethyl) amine) | Cu, Ni, Zn | Histidine, Tryptophan (Trp), possibly Proline (Pro) |
| alkyl mercaptans (i.e., $HS—(CH_2)_7—CH_3$; $HS—(CH_2)_{11}—CH_3$). | Hydrophobic interactions | Phenylalanine (Phe), Leucine (Leu) |

TABLE 1-continued

Library of ligand linkers based upon chelating derivatives with hydrophobic, thiophilic, and covalent interactions.

| Bifunctional Reagent | Affinity Group/Interaction | Amino Acid Residue Interaction |
|---|---|---|
| Thiophilic ligands.($—CH_2—CH_2—SO_2—CH_2—CH_2—S—CH_2—CH_2OH$) | Thiophilic Interactions. | aromatic amino acid side chains, with a relative interaction strength in the order Trp > Tyr > Phe (electron donors). |
| Oxirane gold derivatives | Covalent interaction between gold pads and amino and thio groups in amino acid residues | Amino/thiol containing residues Cysteine (Cys), Lysine (Lys). |

(b) Functionalizing γ Tubulin

The nucleating protein, GST-γ-Tubulin, is a fusion protein in which an N-terminal GST (Glutathione S-Transferase) sequence is joined to γ-Tubulin. Glutathione binds the GST protein and serves as a linker to the γ-Tubulin; Glutathione acts as a ligand. An immunoglobulin specific for the γ-Tubulin, which immunoglobulin bears a fluorescent moiety (IgG-Cy3), is used to demonstrate the formation of the Gold/FSAM/Fusion-Protein complex. Strong fluorescence from a functionalized gold electrode on a Silicon Oxide substrate, coated with the FSAM/Fusion-Protein indicates that this complex binds selectively to the gold surface and not the background of benign (nonfunctionalized) Silicon Oxide. (See FIG. 2B for further details.)

Figure 2A:
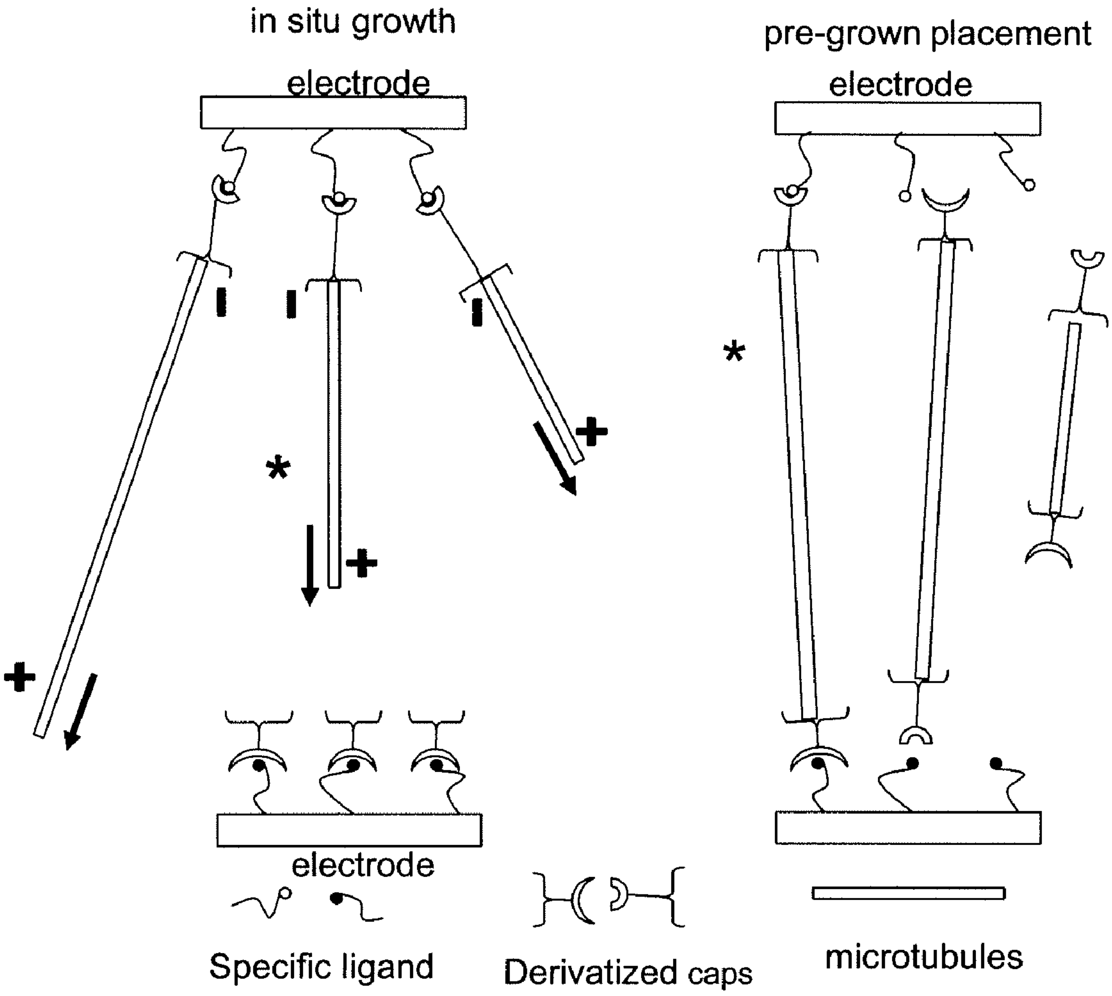
FIG. 2A: Is a schematic illustration of nano-interconnection between two test pads by in situ formation of microtubules (in situ growth) as described herein or pre-grown and stabilized MTs (pre-grown placement). Specific linker/ligand chemistries mediate MT connection to the test pads (details described herein below). * denotes interconnecting MT.

Controlled Nucleation and Growth of Microtubules from the GST/γ-Tubulin Fusion Protein In-vitro MT assembly is performed in PEM 80 buffer at pH ~6.9, with a final concentration of 1.5 mg/ml Tubulin. Polymerization commences by the addition of GTP. Taxol is added as a stabilizing agent during polymerization. Other small organic molecules that inhibit the disassembly of MTs can also be used as stabilizing agents, as can MAPs that bind to the length of the MT. Immersion of the functionalized electrodes into a solution containing both α and β Tubulin leads to the nucleation and assembly of Microtubules from one electrode to the other (as shown in FIG. 2A). This process results in MTs that are attached, and also results in the growth of MTs from the electrodes, so that they can be subsequently aligned and directed by flow, or by any other means, over the gold surface.

The tubulins in this invention, α, β and γ-tubulin, may be from any species and is not limited to human as the proteins are well conserved among various species and provide the required structural template base for metallization to make the interconnects.

Metallization of Microtubules

Metallization of microtubules can in general be accomplished by any art-known method. However it is preferred to use a biologically-compatible benign chemistry through methods of electroless deposition. Copper metallization is particularly useful in preparation of the nanoscale electrical interconnects to this invention. One aspect of this invention that is described in more detail below provides a biologically-compatible metallization method, which functions to metallize MTs, as well as other biological macromolecules and structures, and which is particularly useful for metallization with copper.

The entire process components as described above for making a bio-based interconnect are shown in the following process flow diagram (Scheme 1).

Scheme 1

| PROCESS | COMPONENT | CHEMISTRY |
|---|---|---|
| Grow and purify Recombinant Glutathione S-Transferase/γ-Tubulin Nucleating Protein, Also grow GST/α-Tubulin | 1 | 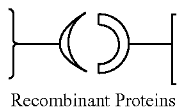 Recombinant Proteins |
| Activate Glutathione Alkanethiol moiety | | 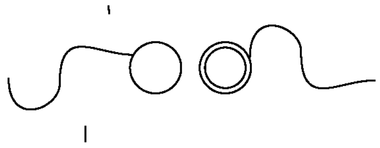 Specific ligand |

-continued
| Scheme 1 | | |
|---|---|---|
| PROCESS | COMPONENT | CHEMISTRY |
| Bind Glutathione alkylthiol conjugates to Gold | | 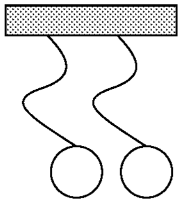 |
| Bind Glutathione alkylthiol conjugate with Recombinant Protein (GST/γ-Tubulin) and GST/α-Tubulin | 2 Examples | 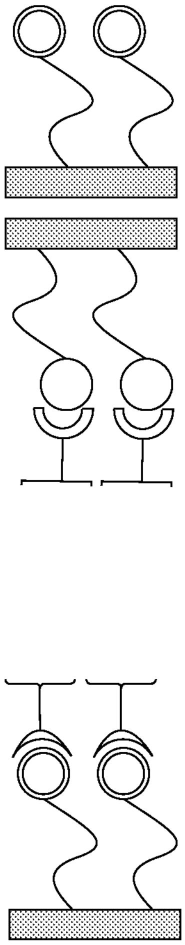 |

-continued

Scheme 1

| PROCESS | COMPONENT | CHEMISTRY |
| --- | --- | --- |
| Grow Tubulin from γ-Tubulin to the α-Tubulin side<br>Stabilize Microtubules with Taxol | 3 | 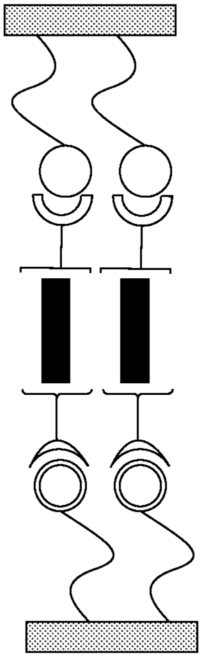 |
| Plate microtubules with copper by electrodes deposition | 4 | 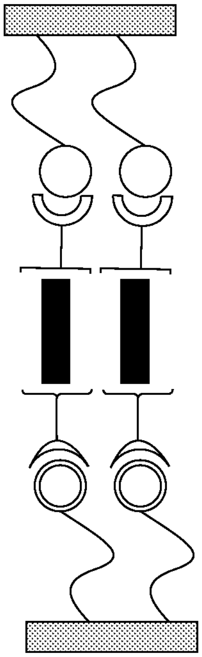 |

In another aspect of the invention a method for metallizing biological macromolecules or structures, and particularly MTs, using a biologically benign electroless deposition chemistry to form nanoscale conductive wires or related structures, useful for forming nanoscale electrical interconnects. The method is particularly useful for metallization with copper.

The terms biological macromolecules or structures is used broadly herein to refer to macromolecules (polymers or aggregates) comprising any one or more type of biological molecule (i.e., peptides, proteins, saccharides, lipids, nucleic acids, etc). The term is more typically used to refer to macromolecules that composed of multiple subunits which are associated with each other through covalent or more typically non-covalent interaction. Typically, such macromolecules define a particular structures, such as fiber, tubule and the like). Macromolecules and structures are typically sub-cellular in size. For purposes herein, biological structures are intended to include viruses and portions thereof. Biological macromolecules and structures, include among others, microtubules and actin filaments, intermediate filaments, collagen fibers, fibrin, alpha-helical polypeptides, flagella, cilia, pili, fibrils, as well as viruses (e.g., tobacco mosaic virus (TMV) or parts thereof (e.g., viral tail fibers).

Typically, prior art metallization of MTs has involved a two step process of activating the MT surface with a noble metal such as Pd or Pt, which is a catalyst for the second step, the electroless deposition of the desired metal. For nickel plating, a bath containing DMAB as the reducing agent was used. Carried out under physiological conditions, temperature range of 30-60° C. and pH between 6 and 8, the metallization process produced nickel only in areas where the Pd catalysts were deposited. While Pd and Pt ions have the capability to diffuse through the MT wall, no deposition was observed on the inner channel due to the rapid metal deposition on the outer surface which blocked ion penetration. Nickel nanowires had an overall diameter of 50 to 60 nm. Similar results were found for cobalt metallization [R. Kirsch, M. Mertig, W. Pompe, R. Wahl, G. Sadowski, K. J. Böhm, and E. Unger, Thin Solid Films 1997, 305, 248. and M. Mertig, R. Kirsch, W. Pompe, Applied Physics A 1998, 66, S723.]. MTs have also been metalized with Pd. The proposed mechanism for the binding of Pd particles was the interaction of the ions with histidine amino acids on the surface. The surface of the MTs was covered with palladium particles of 2 to 3 nm to form quasi-continuous coverage up to 100 nm in diameter [S. Behrens, K. Rahn, W. Habicht, K. J. Böhm, H. Rösner, E. Dinjus, E. Unger, Adv. Mater. 2002, 14(22), 1621].

Copper metallization of templates to produce nanostructures is of particular interest to the semiconductor industry, because copper is currently the interconnect metal of choice in integrated circuits. Copper is a more desirable metal than nickel or cobalt due to its lower resistivity. While there is currently no published work demonstrating the copper plating of microtubules, there is one report on the interaction of copper plating on bolaamphiphile nanotubes. Electroless deposition of copper onto the surface of biological macromolecules, such as MTs, poses a significant challenge, because the commercially available Cu plating baths contain formaldehyde as a reducing agent, and the plating conditions are typically carried out at alkaline pH values (11.5 to 13) and temperatures from 55° C. to 70° C. [Y. Shacham-Diamand, J. Micromech. Microengr., 1991, 1, 66] which are not conducive to retention of biological structures.

The metallization process of this invention is performed by contacting the MTs with metallization components in a metallization solution or liquid (such as a gel). The metallization solution contains a reducible metal salt, and a reducing agent that will reduce the reducible metal. The metallization solution can optionally contain a complexant. The pH of the metallization solution is adjusted to obtain metal deposition on the MTs (rather than metal oxide deposition) at a practical rate without significant depolymerization or denaturization of the MTs.

Because metallization is conducted under biologically benign conditions, there is no need to fix or crosslink the MTs prior to metallization. Further, the method does not require activation of the MT surface with a noble metal such as Pd or Pt. Metallization can be conducted in the presence of a stabilizing agent which stabilizes the MT structure. Suitable MT stabilizing agents include taxol and MAPs (microtubule-associated proteins) among other MT stabilizing agents which are known in the art. MAPs bind to the exterior surface of the microtubules to increase polymerization and stability [K. Kinoshita, I. Arnal, A. Desai, D. N. Drechsel and A. A. Hyman, Science 2001, 294, 1340.]. A previous study has shown that MAP-stabilized MTs are useful for metallizing MTs with Ni [Y. Yang et al, Journal of Materials Science 2004, 39, 1927].

The basic components of the electroless plating bath are: a salt or complex of a reducible metal (such as noble metals and transition metals, including among others Cu, Au and Ag), and the driving force for the metallization, a reducing agent (any suitable reducing agent can be employed and is selected based at least in part on the metal to be reduced). Useful reducing agents include ascorbic acid, mixtures of ascorbic acid and NADH. Choice of reducing agent is important for retaining biologically benign metallization conditions (pH and temperature that do not destabilize the biological template). Ascorbic acid (which can be used in the form of ascorbate salts) and reducing agents having properties similar thereto can be employed. Other additives may include complexants (complexing agents) and stabilizers. Complexants are used to prevent precipitation of metal salts and limit the free metal ions in solution whereas stabilizers control the plating rate and prevent decomposition of solution. Useful complexants include organic acids or salts thereof, organic amines or salts thereof, chelating agents such as EDTA, and hydroxylamine. One of ordinary skill in the art in view of the teachings herein can selected suitable reducible metal salts, suitable reducing agents, and suitable complexants to achieve metallization of biological macromolecules and biological structures. One of ordinary skill in the art using routine experimentation develop variant metallization solutions based on the teachings herein and what is generally known in the art. One of ordinary skill in the art can using the teachings herein and what is generally known in the art adapt the specific methods disclosed herein for metallization of MTs with metals other than copper, particularly gold and silver. The methods specifically disclosed herein can be readily adapted to metalize MTs and other biological macromolecules, particularly protein-containing structures, that are free in solution or that are attached to a substrate. Substrates suitable for immobilization or attachment of biological macromolecules or structures are well known in the art and include, silicon wafers, carbon supports, aminosilane-treated silica, polylysine-coated glass, and metal grids and disks (e.g., Ni grids and disks, gold electrode pads), synthetic polymer supports, polystyrene, agarose, nitrocellulose, and nylon, ITEM grids and electrodes.

Metallization using the method of this invention can result in metalized MTs which can function as nanowires. In general, the methods herein can be used to generate nanowires with diameters ranging from 10 to 100 nm. Metallization for shorter times (~1 minute) produces uniform small-diameter nanowires (diameter of approximately 15 nm). The small diameters observed at short metallization times suggest that metallization can be initiated selectively from the inner surface of the microtubule. The metallization method also provides control over the diameter of the nanowires formed by varying the exposure time of the MTs to the metallization components or solutions. More than one sequential metallization step can be applied to a biological macromolecule or structure to obtain multiple layers of deposited metal.

Metallization is stopped by discontinuing contact with the metalizing components or solution. This can be done by any method, including physical removal, dilution, washing and the like. Metalized structures can be washed using any suitable method to remove residual metallization components or solution.

The metallization method of this invention is particularly suitable for metallization with copper. In this case a preferred copper salt is copper (II) sulfate, preferred reducing agents are ascorbate or a mixture of ascorbate and NADH, a preferred complexant is acetic acid (acetate) and the metallization is preferably carried out at pH of 4 for times ranging from 1 minute to about 5 minutes. In this specific preferred embodiment, pH control of the metallization solution is important to obtain a practical rate of MT metallization.

Cu-metallization of MTs for shorter times (~1-2 minutes) was shown to produce uniform copper wire with diameters of approximately 15 nm, indicating that Cu-metallization is initiated selectively from the inner core of the tubule. It is believe that Cu associates with histidine residues which are found on the inner core of the tubule.

The metallization method of this invention is suitable for metallization of a variety of biological macromolecules and structures. It is particularly suitable for metallization of protein-containing structures, particularly those which contain a plurality of protein subunits, and more particularly those that contain an ordered protein-containing structure, including microtubules, actin filaments and the like. The method is particularly useful for metallization of such species with copper. Other macromolecules, particularly those having elongated forms similar to microtubules, such as polynucleic acids or artificial chromosomes, can also be substrates for electroless plating methods of this invention.

THE EXAMPLES

Example 1

Cloning and Expression of Tubulin

We designed and cloned a γ-tubulin fusion protein could be used to initiate microtubule growth in a precise fashion, especially after attachment to a surface of interest. Additional details of the experiments conducted can be found in Yang et al. (2006) Biotechnology Progress 22: 303-312, which is incorporated by reference herein in its entirety.

Analysis of all of the known human γ-tubulin sequences allowed the design of specific oligonucleotides (oligos) that could then be used as primers in polymerase chain reaction (PCR) to clone γ-tubulin. In addition, those oligos that were designed to be used to PCR amplify the γ-tubulin would also provide the recombinant form with sequences that allow it to be made as a recombinant fusion with glutathione —S— transferase (GST) sequence tag. Specifically, the human sequence that was used to design primers was from NCBI (NM_001070, *Homo sapiens* tubulin, γ-1, TUBG1). They are:

```
5'-GGAATTCTGCCGAGGGAAATCATCACC-3'    (SEQ ID NO: 1)
5'-AAGCTTCACTGCTCCTGGGTGCCCCAGG-3'   (SEQ ID NO: 2)
5'-ACCACGGTCCTGGATGTCATGAGG-3')      (SEQ ID NO: 3)
5'-TCTCGGCCTGTGGACACCATCACG-3'       (SEQ ID NO: 4)
```

These oligonucleotides were then used in PCR to create two fragments of the recombinant γ-tubulin DNA. These were DNA sequenced and then connected to each other appropriately to form the entire recombinant γ-tubulin coding sequence. Sequence analysis shows that they are most likely TUBG1, but are slightly different.

```
γ tubulin Clone 1 (SEQ ID NO: 5)
GGAATTggaattctgc cgagggaaat catcacccta cagttgggcc
agtgcggcaa tcagattggg ttcgagttct ggaaacagct
gtgcgccgag catggtatca gccccgaggg catcgtggag
gagttcgcca ccgagggcac tgaccgcaag gacgtctttt
tctaccaggc agacgatgag cactacatcc cccgggccgt
gctgctggac ttggaacccc gggtgatcca ctccatcctc
aactccccct atgccaagct ctacaaccca gagaacatct
acctgtcgga acatggagga ggagctggca acaactgggc
cagcggattc tcccagggag aaaagatcca tgaggacatt
tttgacatca tagaccggga ggcagatggt agtgacagtc
tagagggctt tgtgctgtgt cactccattg ctgggggac
aggctctgga ctgggttcct acctcttaga acggctgaat
gacaggtatc ctaagaagct ggtgcagaca tactcagtgt
ttcccaacca ggacgagatg agcgatgtgg tggtccagcc
ttacaattca ctcctcacac tcaagaggct gacgcagaat
gcagactgtg tggtggtgct ggacaacaca gccctgaacc
ggattgccac agaccgcctg cacatccaga acccatcctt
ctcccagatc aaccagctgg tgtctaccat catgtcagcc
agcaccacca ccctgcgcta ccctggctac atgaacaatg
acctcatcgg cctcatcgcc tcgctcattc ccaccccacg
gctccacttc ctcatgaccg gctacacccc tctcactacg
gaccagtcag tggccagcgt gaggaagacc acggtcctgg
atgtcatgag gcggctgctg cagcccaaga acgtgatggt
gtccacaggc cgaga
```

```
γ tubulin Clone 2 (SEQ ID NO: 6)
accacggtcc tggatgtcat gaggcggctg ctgcagccca
agaacgtgat ggtgtccaca ggccgagacc gccagaccaa
ccactgctac atcgccatcc tcaacatcat ccagggagag
gtggacccca cccaggtcca caagagcttg cagaggatcc
gggaacgcaa gttggccaac ttcatcccgt ggggccccgc
cagcatccag gtggccctgt cgaggaagtc tccctacctg
ccctcggccc accgggtcag cgggctcatg atggccaacc
acaccagcat ctcctcgctc ttcgagagaa cctgtcgcca
gtatgacaag ctgcgtaagc gggaggcctt cctggagcag
ttccgcaagg aggacatgtt caaggacaac tttgatgaga
tggacacatc cagggagatt gtgcagcagc tcatcgatga
gtaccatgcg gccacacggc cagactacat ctcctggggc
acccaggagc agtgaAGCTT
```

```
γ tubulin clone 3 (SEQ ID NO: 7, ligation product
of clone 1 and clone 2)
ggaattctgc cgagggaaat catcacccta cagttgggcc
agtgcggcaa tcagattggg ttcgagttct ggaaacagct
gtgcgccgag catggtatca gccccgaggg catcgtggag
gagttcgcca ccgagggcac tgaccgcaag gacgtctttt
tctaccaggc agacgatgag cactacatcc cccgggccgt
gctgctggac ttggaacccc gggtgatcca ctccatcctc
aactccccct atgccaagct ctacaaccca gagaacatct
acctgtcgga acatggagga ggagctggca acaactgggc
cagcggattc tcccagggag aaaagatcca tgaggacatt
tttgacatca tagaccggga ggcagatggt agtgacagtc
tagagggctt tgtgctgtgt cactccattg ctgggggggac
aggctctgga ctgggttcct acctcttaga acggctgaat
gacaggtatc ctaagaagct ggtgcagaca tactcagtgt
ttcccaacca ggacgagatg agcgatgtgg tggtccagcc
ttacaattca ctcctcacac tcaagaggct gacgcagaat
gcagactgtg tggtggtgct ggacaacaca gccctgaacc
ggattgccac agaccgcctg cacatccaga acccatcctt
ctcccagatc aaccagctgg tgtctaccat catgtcagcc
agcaccacca ccctgcgcta ccctggctac atgaacaatg
acctcatcgg cctcatcgcc tcgctcattc ccaccccacg
gctccacttc ctcatgaccg gctacacccc tctcactacg
gaccagtcag tggccagcgt gaggaagacc acggtcctgg
atgtcatgag gcggctgctg cagcccaaga acgtgatggt
gtccacaggc cgagaccgcc agaccaacca ctgctacatc
gccatcctca acatcatcca gggagaggtg gaccccaccc
aggtccacaa gagcttgcag aggatccggg aacgcaagtt
ggccaacttc atcccgtggg gccccgccag catccaggtg
gccctgtcga ggaagtctcc ctacctgccc tcggcccacc
gggtcagcgg gctcatgatg gccaaccaca ccagcatctc
ctcgctcttc gagagaacct gtcgccagta tgacaagctg
cgtaagcggg aggccttcct ggagcagttc cgcaaggagg
acatgttcaa ggacaacttt gatgagatgg acacatccag
ggagattgtg cagcagctca tcgatgagta ccatgcggcc
acacggccag actacatctc ctggggcacc caggagcagt
gaagctt
```

The recombinant γ-tubulin DNA was then cloned into pGEX-KG (Guan and Dixon. 1991. Anal. Biochem. 192:262-267) to create the final clone, pGEXTUBG, which is then used to express recombinant GST-tagged γ-tubulin protein. The complete sequence (SEQ ID NO:8) of that pGEXTUBG clone is provided herein.

```
pGEXTUBG (SEQ ID NO: 8)
acgttatcga ctgcacggtg caccaatgct tctggcgtca
ggcagccatc ggaagctgtg gtatggctgt gcaggtcgta
aatcactgca taattcgtgt cgctcaaggc gcactcccgt
tctggataat gtttttttgcg ccgacatcat aacggttctg
gcaaatattc tgaaatgagc tgttgacaat taatcatcgg
ctcgtataat gtgtggaatt gtgagcggat aacaatttca
cacaggaaac agtattcatg tcccctatac taggttattg
gaaaattaag ggccttgtgc aacccactcg acttcttttg
gaatatcttg aagaaaaata tgaagagcat ttgtatgagc
gcgatgaagg tgataaatgg cgaaacaaaa agtttgaatt
gggtttggag tttcccaatc ttccttatta tattgatggt
gatgttaaat taacacagtc tatggccatc atacgttata
tagctgacaa gcacaacatg ttgggtggtt gtccaaaaga
gcgtgcagag atttcaatgc ttgaaggagc ggttttggat
attagatacg gtgtttcgag aattgcatat agtaaagact
ttgaaactct caaagttgat ttttcttagca agctacctga
aatgctgaaa atgttcgaag atcgtttatg tcataaaaca
tatttaaatg gtgatcatgt aacccatcct gacttcatgt
tgtatgacgc tcttgatgtt gttttataca tggacccaat
gtgcctggat gcgttcccaa aattagtttg ttttaaaaaa
cgtattgaag ctatcccaca aattgataag tacttgaaat
ccagcaagta tatagcatgg cctttgcagg gctggcaagc
cacgtttggt ggtggcgacc atcctccaaa atcggatctg
gttccgcgtg gatccccggg aatttccggt ggtggtggtg
gaattctgcc gagggaaatc atcaccctac agttgggcca
gtgcggcaat cagattgggt tcgagttctg gaaacagctg
tgcgccgagc atggtatcag ccccgagggc atcgtggagg
agttcgccac cgagggcact gaccgcaagg acgtcttttt
ctaccaggca gacgatgagc actacatccc ccgggccgtg
ctgctggact tggaaccccg ggtgatccac tccatcctca
actcccccta tgccaagctc tacaacccag agaacatcta
cctgtcggaa catggaggag gagctggcaa caactgggcc
agcggattct cccagggaga aaagatccat gaggacattt
ttgacatcat agaccgggag gcagatggta gtgacagtct
agagggcttt gtgctgtgtc actccattgc tgggggggaca
ggctctggac tgggttccta cctcttagaa cggctgaatg
acaggtatcc taagaagctg gtgcagacat actcagtgtt
tcccaaccag gacgagatga gcgatgtggt ggtccagcct
tacaattcac tcctcacact caagaggctg acgcagaatg
cagactgtgt ggtggtgctg gacaacacag ccctgaaccg
```

-continued gattgccaca gaccgcctgc acatccagaa cccatccttc
tcccagatca accagctggt gtctaccatc atgtcagcca
gcaccaccac cctgcgctac cctggctaca tgaacaatga
cctcatcggc ctcatcgcct cgctcattcc caccccacgg
ctccacttcc tcatgaccgg ctacacccct ctcactacgg
accagtcagt ggccagcgtg aggaagacca cggtcctgga
tgtcatgagg cggctgctgc agcccaagaa cgtgatggtg
tccacaggcc gagaccgcca gaccaaccac tgctacatcg
ccatcctcaa catcatccag ggagaggtgg accccaccca
ggtccacaag agcttgcaga ggatccggga acgcaagttg
gccaacttca tcccgtgggg ccccgccagc atccaggtgg
ccctgtcgag gaagtctccc tacctgccct cggcccaccg
ggtcagcggg ctcatgatgg ccaaccacac cagcatctcc
tcgctcttcg agagaacctg tcgccagtat gacaagctgc
gtaagcggga ggccttcctg gagcagttcc gcaaggagga
catgttcaag gacaactttg atgagatgga cacatccagg
gagattgtgc agcagctcat cgatgagtac catgcggcca
cacggccaga ctacatctcc tggggcaccc aggagcagtg
aagcttattc atcgtgactg actgacgatc tgcctcgcgc
gtttcggtga tgacggtgaa aacctctgac acatgcagct
cccggagacg gtcacagctt gtctgtaagc ggatgccggg
agcagacaag cccgtcaggg cgcgtcagcg ggtgttggcg
ggtgtcgggg cgcagccatg acccagtcac gtagcgatag
cggagtgtat aattcttgaa gacgaaaggg cctcgtgata
cgcctatttt tataggttaa tgtcatgata ataatggttt
cttagacgtc aggtggcact tttcggggaa atgtgcgcgg
aacccctatt tgtttatttt tctaaataca ttcaaatatg
tatccgctca tgagacaata accctgataa atgcttcaat
aatattgaaa aaggaagagt atgagtattc aacatttccg
tgtcgccctt attccctttt ttgcggcatt ttgccttcct
gtttttgctc acccagaaac gctggtgaaa gtaaaagatg
ctgaagatca gttgggtgca cgagtgggtt acatcgaact
ggatctcaac agcggtaaga tccttgagag ttttcgcccc
gaagaacgtt ttccaatgat gagcactttt aaagttctgc
tatgtggcgc ggtattatcc cgtgttgacg ccgggcaaga
gcaactcggt cgccgcatac actattctca gaatgacttg
gttgagtact caccagtcac agaaaagcat cttacggatg
gcatgacagt aagagaatta tgcagtgctg ccataaccat
gagtgataac actgcggcca acttacttct gacaacgatc
ggaggaccga aggagctaac cgcttttttg cacaacatgg -continued gggatcatgt aactcgcctt gatcgttggg aaccggagct
gaatgaagcc ataccaaacg acgagcgtga caccacgatg
cctgcagcaa tggcaacaac gttgcgcaaa ctattaactg
gcgaactact tactctagct tcccggcaac aattaataga
ctggatggag gcggataaag ttgcaggacc acttctgcgc
tcggcccttc cggctggctg gtttattgct gataaatctg
gagccggtga gcgtgggtct cgcggtatca ttgcagcact
ggggccagat ggtaagccct cccgtatcgt agttatctac
acgacgggga gtcaggcaac tatggatgaa cgaaatagac
agatcgctga gataggtgcc tcactgatta agcattggta
actgtcagac caagtttact catatatact ttagattgat
ttaaaacttc atttttaatt taaaaggatc taggtgaaga
tcctttttga taatctcatg accaaaatcc cttaacgtga
gttttcgttc cactgagcgt cagaccccgt agaaaagatc
aaaggatctt cttgagatcc tttttttctg cgcgtaatct
gctgcttgca aacaaaaaaa ccaccgctac cagcggtggt
ttgtttgccg gatcaagagc taccaactct ttttccgaag
gtaactggct tcagcagagc gcagatacca aatactgtcc
ttctagtgta gccgtagtta ggccaccact tcaagaactc
tgtagcaccg cctacatacc tcgctctgct aatcctgtta
ccagtggctg ctgccagtgg cgataagtcg tgtcttaccg
ggttggactc aagacgatag ttaccggata aggcgcagcg
gtcgggctga acggggggtt cgtgcacaca gcccagcttg
gagcgaacga cctacaccga actgagatac ctacagcgtg
agctatgaga aagcgccacg cttcccgaag ggagaaaggc
ggacaggtat ccggtaagcg gcagggtcgg aacaggagag
cgcacgaggg agcttccagg gggaaacgcc tggtatcttt
atagtcctgt cgggtttcgc cacctctgac ttgagcgtcg
atttttgtga tgctcgtcag gggggcggag cctatggaaa
aacgccagca acgcggcctt tttacggttc ctggcctttt
gctggccttt tgctcacatg ttctttcctg cgttatcccc
tgattctgtg gataaccgta ttaccgcctt tgagtgagct
gataccgctc gccgcagccg aacgaccgag cgcagcgagt
cagtgagcga ggaagcggaa gagcgcctga tgcggtattt
tctccttacg catctgtgcg gtatttcaca ccgcataaat
tccgacacca tcgaatggtg caaaaccttt cgcggtatgg
catgatagcg cccggaagag agtcaattca gggtggtgaa
tgtgaaacca gtaacgttat acgatgtcgc agagtatgcc
ggtgtctctt atcagaccgt ttcccgcgtg gtgaaccagg
ccagccacgt ttctgcgaaa acgcgggaaa aagtggaagc -continued

```
ggcgatggcg gagctgaatt acattcccaa ccgcgtggca

caacaactgg cgggcaaaca gtcgttgctg attggcgttg

ccacctccag tctggccctg cacgcgccgt cgcaaattgt

cgcggcgatt aaatctcgcg ccgatcaact gggtgccagc

gtggtggtgt cgatggtaga acgaagcggc gtcgaagcct

gtaaagcggc ggtgcacaat cttctcgcgc aacgcgtcag

tgggctgatc attaactatc cgctggatga ccaggatgcc

attgctgtgg aagctgcctg cactaatgtt ccggcgttat

ttcttgatgt ctctgaccag acacccatca acagtattat

tttctcccat gaagacggta cgcgactggg cgtggagcat

ctggtcgcat tgggtcacca gcaaatcgcg ctgttagcgg

gcccattaag ttctgtctcg gcgcgtctgc gtctggctgg

ctggcataaa tatctcactc gcaatcaaat tcagccgata

gcggaacggg aaggcgactg gagtgccatg tccggttttc

aacaaaccat gcaaatgctg aatgagggca tcgttcccac

tgcgatgctg gttgccaacg atcagatggc gctgggcgca

atgcgcgcca ttaccgagtc cgggctgcgc gttggtgcgg

atatctcggt agtgggatac gacgataccg aagacagctc

atgttatatc ccgccgttaa ccaccatcaa acaggatttt

cgcctgctgg ggcaaaccag cgtggaccgc ttgctgcaac

tctctcaggg ccaggcggtg aagggcaatc agctgttgcc

cgtctcactg gtgaaaagaa aaaccaccct ggcgcccaat

acgcaaaccg cctctccccg cgcgttggcc gattcattaa

tgcagctggc acgacaggtt tcccgactgg aaagcgggca

gtgagcgcaa cgcaattaat gtgagttagc tcactcatta

ggcaccccag gctttacact ttatgcttcc ggctcgtatg

ttgtgtggaa ttgtgagcgg ataacaattt cacacaggaa

acagctatga ccatgattac ggattcactg gccgtcgttt

tacaacgtcg tgactgggaa aaccctggcg ttacccaact

taatcgcctt gcagcacatc ccccttttcgc cagctggcgt

aatagcgaag aggcccgcac cgatcgccct tcccaacagt

tgcgcagcct gaatggcgaa tggcgctttg cctggtttcc

ggcaccagaa gcggtgccgg aaagctggct ggagtgcgat

cttcctgagg ccgatactgt cgtcgtcccc tcaaactggc

agatgcacgg ttacgatgcg cccatctaca ccaacgtaac

ctatcccatt acggtcaatc cgccgtttgt tcccacggag

aatccgacgg gttgttactc gctcacattt aatgttgatg

aaagctggct acaggaaggc cagacgcgaa ttatttttga

tggcgttgga att
```

The GST coding sequence starts at the underlined 'atg' and ends at the underlined Eco RI site (gaattc). The γ-tubulin sequence starts at this engineered Eco RI site and terminates with a "tga" just before an engineered Hind III site (aagctt, underlined). In addition, the start codon for γ-tubulin (atg) was mutated to a Leu codon (ctg). The underlined 'tga' sequence is the translation stop codon. Proteins were expressed in recombinant *E. coli* and purified using an affinity column that specifically binds the GST-γ-Tubulin protein. Unbound proteins were washed from the column, and the purified GST-γ-Tubulin protein was eluted using free glutathione. Protein purity was verified using SDS-PAGE; the eluted protein of 85 kDa was of the correct size. The protein was also verified immunologically using ELISA, with antibodies highly specific to GST and γ-Tubulin.

As an alternative to immobilization of the nucleation protein to the surface via a GST tag, a His-tagged γ-tubulin was produced recombinantly. The sequence encoding the His-tagged γ-tubulin is given in SEQ ID NO:9.

```
gtuHis complete sequence (SEQ ID NO: 9)
ATGCCGAGGGAAATCATCACCCTACAGTTGGGCCAGTGCGGCAATCAGAT

TGGGTTCGAGTTCTGGAAACAGCTGTGCGCCGAGCATGGTATCAGCCCCG

AGGGCATCGTGGAGGAGTTCGCCACCGAGGGCACTGACCGCAAGGACGTC

TTTTTCTACCAGGCAGACGATGAGCACTACATCCCCCGGGCCGTGCTGCT

GGACTTGGAACCCCGGGTGATCCACTCCATCCTCAACTCCCCCTATGCCA

AGCTCTACAACCCAGAGAACATCTACCTGTCGGAACATGGAGGAGGAGCT

GGCAACAACTGGGCCAGCGGATTCTCCCAGGGAGAAAAGATCCATGAGGA

CATTTTTGACATCATAGACCGGGAGGCAGATGGTAGTGACAGTCTAGAGG

GCTTTGTGCTGTGTCACTCCATTGCTGGGGGGACAGGCTCTGGACTGGGT

TCCTACCTCTTAGAACGGCTGAATGACAGGTATCCTAAGAAGCTGGTGCA

GACATACTCAGTGTTTCCCAACCAGGACGAGATGAGCGATGTGGTGGTCC

AGCCTTACAATTCACTCCTCACACTCAAGAGGCTGACGCAGAATGCAGAC

TGTGTGGTGGTGCTGGACAACACAGCCCTGAACCGGATTGCCACAGACCG

CCTGCACATCCAGAACCCATCCTTCTCCCAGATCAACCAGCTGGTGTCTA

CCATCATGTCAGCCAGCACCACCACCCTGCGCTACCCTGGCTACATGAAC

AATGACCTCATCGGCCTCATCGCCTCGCTCATTCCCACCCCACGGCTCCA

CTTCCTCATGACCGGCTACACCCCTCTCACTACGGACCAGTCAGTGGCCA

GCGTGAGGAAGACCACGGTCCTGGATGTCATGAGGCGGCTGCTGCAGCCC

AAGAACGTGATGGTGTCCACAGGCCGAGACCGCCAGACCAACCACTGCTA

CATCGCCATCCTCAACATCATCCAGGGAGAGGTGGACCCCACCCAGGTCC

ACAAGAGCTTGCAGAGGATCCGGGAACGGAAGTTGGCCAACTTCATCCCG

TGGGGCCCCGCCAGCATCCAGGTGGCCCTGTCGAGGAAGTCTCCCTACCT

GCCCTCGGCCCACCGGGTCAGCGGGCTCATGATGGCCAACCACACCAGCA

TCTCCTCGCTCTTCGAGAGAACCTGTCGCCAGTATGACAAGCTGCGTAAG

CGGGAGGCCTTCCTGGAGCAGTTCCGCAAGGAGGACATGTTCAAGGACAA

CTTTGATGAGATGGACACATCCAGGGAGATTGTGCAGCAGCTCATCGATG

AGTACCATGCGGCCACACGGCCAGACTACATCTCCTGGGGCACCCAGGAG

CAGGGAGGAGGAGGAGGACTCGAGCACCACCACCACCAC
```

The final purification yielded the fusion protein which had a final concentration of about 4-5 μM and a purification of greater than 80%.

For use in extension of microtubules from an immobilized γ-Tubulin or γ-Tubulin nucleation complex on a surface of interest, tubulin preparations containing α-tubulin and β-tubulin are obtained from commercial sources (e.g., Cytoskeleton Inc., Denver, Colo.).

Recombinant GST-alpha tubulin has also been produced for use in the present invention. Alpha tubulin was selected as a protein for the capping of the growing (plus) ends of microtubules and for the "capture of a microtubule at a discrete position on the surface. This protein was selected since it participates in attachment to beta tubulin at the plus end of the microtubule, as well as interacting with alpha tubulin molecules laterally.

Alpha tubulin was attached to a GST tag sequence via a glycine linker consisting of 15 glycine molecules. To create this, total RNA was isolated from human fibroblasts, and cDNA was made using RT-PCR. Since the alpha tubulin gene was quite long (1350 base pairs) to be amplified by traditional PCR, its sequence was split into two halves, both spanning an EcoRV restriction site, used later to reassemble the two halves.

Because the amino terminus of the protein provides the most accessible end for attachment to GST, a series of primers were designed to elongate the protein with a string of glycine residues. Primers were designed against the human alpha tubulin sequence (Accession number NM_032704) to include the coding region of the gene. The first half of the gene (segment A), bases 101-794 on the mRNA sequence (corresponding to bases 1-694 of the coding region) was engineered with multiple steps. Upstream of the glycine codons, a BamHI site was added to integration into a plasmid. The second half of the gene (segment B), bases 714-1450 on the mRNA sequence (corresponding to bases 614-1350 of the coding region) was engineered with a HindIII restriction site directly following the stop codon, to be used for integration into a plasmid. Each PCR reaction was followed by cloning the gene fragment into the pBlueScript plasmid and transfected into *E. coli*. Plasmids were purified from the *E. Coli* after overnight growth and then the insert was sequenced to make sure that no mutations were introduced into the coding sequence that would hamper protein function.

At each step a clone was selected that contained the correct amino acid coding sequence, corresponding to the published data for α-tubulin. The final cloning step was performed by digestion with HindIII and EcoRV; inserting segment B into a plasmid already containing segment A. The insert so produced was also sequenced and the encoded amino acid sequence was verified. From this, the plasmid was digested with BamHI and HindIII, and cloned into an expression vector containing the GST sequence (pGEX-KG). The entire GST-alpha tubulin clone was then sequenced and verified. Twelve clones were selected, grown, and induced with IPTG to determine which clone had the highest expression of the recombinant GST-α-tubulin. All twelve showed moderate expression levels of the protein, at the appropriate size, with some cleavage into smaller fragments. The cloned segment is further verified by performing an ELISA using anti-alpha tubulin antibody with the recombinantly expressed protein.

Example 2

Surface Functionalization

Figure 2B:
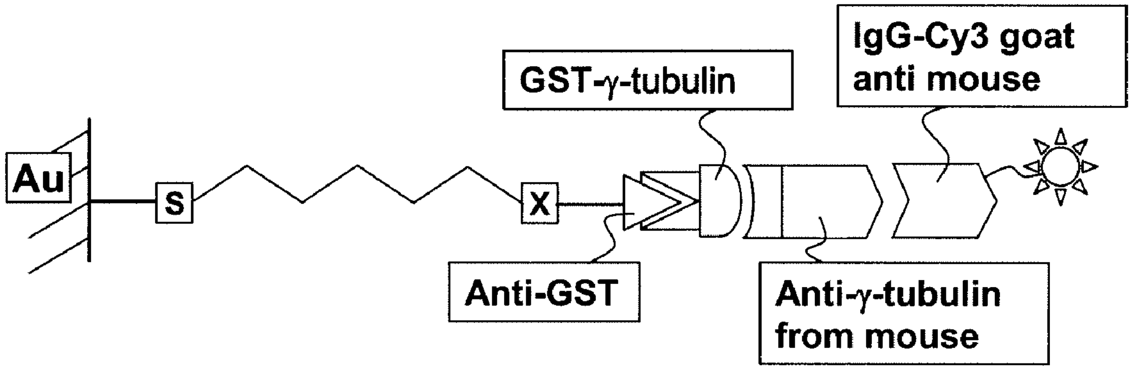
FIG. 2B is a schematic illustration of a functionalized gold surface bound by an FSAM and GST-γ-Tubulin fusion protein. S stands for sulfur and X for carboxylic acid. The fusion protein GST-γ-Tubulin binds to anti-GST. A specific immunoglobulin, designated anti-γ-Tubulin, which binds to the Gold/FSAM/Fusion-Protein complex, bears a fluorescent moiety, IgG-Cy3, and is incorporated as evidence of the FSAM binding to the gold and for the formation of the protein complex.

A protein nucleation method for MT growth from gold substrates has been developed based on the self-assembly of reactive alkanethiols together with the engineered fusion protein. Oxidized silicon wafers were patterned with gold electrodes, followed by treatment with piranha solution to clean organic contaminants and to activate the gold surface. An anti-GST antibody was bound to a SAM of carboxylic acid-terminated alkanethiols on the gold surface through the carboxylic acid group at the end of the alkyl chains (FIG. 2B). Anti-GST is a specific antibody for selective binding of GST attached to recombinant proteins, in our case, the microtubule-nucleating fusion protein, GST-γ-tubulin. Additionally, a specific antibody that binds γ-tubulin is then recognized by a secondary antibody that has a fluorescent tag (IgG-Cy3) and is used to quantify the extent of the formation of the protein assembly. Strong fluorescence from a functionalized gold surface on a $SiO_2$ substrate coated with the fusion protein indicates that the approach we have developed gives a uniform coverage of the electrode.

We have also characterized the morphology of the functionalized gold substrate by atomic force microscopy (AFM). AFM data showed the initial localization of a γ-tubulin functionalized gold surface, and of a pure gold surface. Prior to imaging, the pure gold surface was treated with piranha solution. The gold substrate exhibits some roughness with feature size of approximately 80 to 100 nm. The γ-tubulin localized surface appears to be morphologically similar to that of the gold substrate indicating that the nucleating fusion-protein film binds the substrate.

Example 3

MT Growth

For this study, we used tubulin (>99% pure) prepared from bovine brain extracts and modified with covalently linked fluorescein (Cytoskeleton Inc). The fluorescein-modified tubulin was stored at −70° C. in storage buffer (pH 6.8; 80 mM piperazine-N,N'-bis 2-ethanesulfonic acid sequisodium salt (PIPES), 1 mM magnesium chloride ($MgCl_2$); 1 mM ethylene glycol-bis(b-amino-ethyl ether) N,N,N',N'-tetra-acetic acid (EGTA) and 1 mM guanosine 5'-triphosphate (GTP)).

In-vitro MT assembly was performed in PEM 80 buffer (80 mM PIPES, 1 mM EGTA, 4 mM Magnesium chloride ($MgCl_2$), using KOH to adjust PH to 6.9) using a final concentration of tubulin at 0.25 mg/ml ($2.3\times10^{-6}$ M). Polymerization was initiated by the addition of GTP (final concentration is 0.25 mM) in the presence of taxol (final concentration is 10 μM). Taxol reduces the competing "depolymerization" process.

In order to test the specificity of the interaction between MTs and the γ-tubulin functionalized substrates, we conducted experiments in which MTs were grown in the presence or absence of the functionalized Au surfaces. In the first case, patterned silicon substrates with functionalized Au pads were immersed into the solution during the polymerization process. The solutions, both with and without substrates, were transferred from an ice bath to a heat bath at 37° C. to promote polymerization for a predetermined time. Because the MT concentration is very high in the solution, we analyzed the MT growth dynamics in the solution by diluting it 50 fold into PEM 80 buffer, and immediately fixing the MTs using the same amount of solution of 3% Glutaradehyde for at least 3 minutes. The solution containing the fixed MTs was transferred onto a poly-L-Lysine coated slide for observation. The microchips were pulled out after polymerization, rinsed with PBS buffer for approximately 10 seconds, and fixed using Methanol (−20° C.) for 3 minutes. The microtubules both on the glass slide and on the microchips were examined using immunofluorescence microscopy. Detailed structural information was also obtained by scanning electron microscopy (SEM). The samples were prepared by super critical $CO_2$ drying after fixing the MTs with glutaradehyde (3%) followed by sputtering a thin film of gold.

Microtubules were grown in the presence of two different gold surfaces prepared on hydrophilic oxidized silicon wafers. The gold pads on the first sample were functionalized with the GST-γ-tubulin as a nucleation protein. The gold pads on the second sample were not functionalized, and their immersion in a solution of tubulin served as a control experiment. Sampling of the solution in which the non-functionalized sample was immersed indicated the presence of numerous MTs in suspension; however, none are to be seen on the surface of the non-functionalized substrate. In contrast the functionalized gold pad appeared to be covered with MTs. To rule out direct nonspecific interaction between MTs self-assembled in the solution and the functionalized gold electrodes, we have compared the growth dynamics of MTs grown in solution and of MTs that appear to cover the γ-tubulin-functionalized gold surfaces. Two series of experiments were conducted for different growth times. In the first series we investigated the growth dynamics of the MTs that appear to cover the functionalized gold electrodes. The second series consisted of a study of the growth dynamics of MTs in the absence of functionalized substrate under the same growth conditions. Two polymerization time periods were considered: 5 and 10 min. The length distributions of MTs grown in the presence of a substrate that appear to cover the gold electrodes and the length distribution of MTs nucleated and grown in solution were measured. We report in FIG. 3 A and B the length distribution after 5 and 10 min of polymerization. The experiments that lasted 5 min show trends similar to those that lasted twice as much but of course lower values of the average MT lengths. FIGS. 3A and B show that the functionalized gold pad has a strong influence on the growth dynamics of MTs. The average lengths of MTs grown in solution are approximately 0.62 and 1.11 micrometer after 5 and 10 min of polymerization, respectively. In the presence of functionalized microchips, the average lengths of MTs on the functionalized gold surfaces increased significantly. Comparing the results of the polymerization with and without functionalized microchips, the average MT length increased from 0.62 to 1.68 micron for 5 min of polymerization and increased from 1.11 to 3.47 micron for the longer experiments. This result indicates that the γ-tubulin-functionalized gold surface interacts specifically with MTs, by promoting the nucleation of MTs and their subsequent growth. To verify that MTs growing from the functionalized gold pads are tethered to the γ-tubulin-functionalized gold surface, we have conducted real-time observations of MT growth under a fluorescent microscope. For this experiment we have used a large flat functionalized gold substrate. A droplet of solution containing fluorescein-tubulin was placed directly onto the functionalized gold surface for MT assembly and observed using immuno-fluorescence microscopy. By focusing through different focal planes, MTs were found both on the gold surface and in the solution above the surface. The MTs observed in the proximity of the substrate are anchored by one end to the surface. The microscope is focused on the pad surface thus the segment of the MT nearest to the substrate is in focus. The other end of the MT is blurred and out of focus, indicating that the MT is pointing into the solution. By applying pressure onto the cover slip of the microscope slide, we have induced a shear flow of the solution that drags and aligns the pointing end of the MT in its direction. The end of the MT closest to the substrate does not undergo any displacement showing that the MT is indeed bound to the functionalized gold pad. MTs nucleated and grown from a functionalized surface are shown to be amenable to orientation by fluid flow.

Where capture of the plus end of a MT is desired, there is a cap protein immobilized in a manner analogous to the immobilization (surface functionalization) of the nucleation protein. When the MT is sufficiently long, it will come in contact with and bind to the capture protein, and the MT will then be fixed at both ends to the solid surface.

Example 4

Characterization by Immuno-Fluorescence Microscopy

Immunofluorescence microscopy is used to check the existence and alignment of microtubules either on a glass slide or on the microchips. As described below, it is performed on a rectangular poly-L-lysine coated microscope slide.

First, a small amount of microtubule dilution is transferred to a poly-L-lysine coated microscope slide (MTs dilution: MTs stock solution+PEMTAX) and allowed to stand for 20 minutes at room temperature. Then methanol (−20° C.) is added to the microscope slide so that methanol covers entire surface where microtubule dilution is; it is allowed to stand for 2-3 minutes at −20° C. Then the slide is immersed in the block solution for 20-30 minutes at room temperature. The block solution serves to block all signals from other proteins (Block solution: PBS buffer+0.1 wt % dried skim milk+0.1 wt % BSA). The slide is removed from the block solution; and excess block solution is removed from the slide. Dilution I, the primary antibody, commercially available antibody specific for tubulin, is added to the microscope slide. Dilution I is β-tubulin antibody diluted 1:200 in block solution. It is allowed to stand for 30 minutes at room temperature.

The slide is then immersed in the block solution for 2 minutes to wash off excess dilution I solution and shaken gently at room temperature. The wash and shake steps are repeated twice. Then Dilution II, Cy-3 (secondary antibody, also commercially available) is added to the microscope slide. Dilution II is Cy-3 goat anti-mouse: block solution diluted 1:50 in block solution. The slide is covered with aluminum foil and allowed to stand for 30 minutes. The microscope slide is then immersed in block solution for 2 minutes and shaken gently at room temperature; this is repeated twice. PBS buffer is used to wash one time, for 2 minutes.

Next the poly-L-Lysine coated slide is covered with a cover slip and observed using a fluorescence microscope, with a red color filter and digital camera to take pictures.

The block solution is prepared as follows. The final volume is 100 ml, with the following composition: 1 gm nonfat dry milk, 1-gram bovine albumin (BSA) in PBS buffer; it can be stored for a maximum of 3 days. 1 gm non-fat milk and 1 gm albumin (BSA) are mixed with PBS buffer, and then the volume is adjusted to 100 ml with PBS buffer and mixed well. The block solution is stored at 4° C.

PEM 80 buffer solution is 80 mM PIPES, 1 mM EGTA, and 4 mM MgCl2 in $H_2O$, with KOH (10 N stock) used to adjust the pH of the solution to 6.9. This buffer is filter-sterilized and stored at 4° C.

Example 5

Metallization Experiments

MTs were synthesized from high purity tubulin proteins (>99% tubulin monomers) and MTs with MAPs were obtained from low purity MAP-rich tubulin (~30% MAPs). These tubulin proteins were isolated from bovine brain (Cytoskeleton, Inc.) and stored at −70° C. in G-PEM buffer (pH 6.8). In-vitro MT assembly was performed in a buffer containing PEM80 buffer (80 mM PIPES, 1 mM EGTA, 4 mM $MgCl_2$, using KOH to adjust the pH to 6.9), 10 mM of GTP and 10 mM of taxol. By adding the specific tubulin to the buffer, the MT stock solution was prepared. The final concentration of tubulin in the stock solution was 1.5 mg/ml. Polymerization of the MTs was completed after rotating the solution in an incubator at a low speed of 15 rpm for 30 minutes at 37° C.

Immunolabeling of MTs was used for fluorescence microscopy imaging. MTs were immobilized on a cationic substrate (poly-L-lysine coated glass) and allowed to settle for 20 to 25 minutes. The MTs were initially bathed for 30 minutes in an anti-β-tubulin solution which was the primary antibody (Sigma Inc.). Next, the labeled MTs were contacted for 30 minutes with a secondary antibody directed against mouse IgG with a Cy3 fluorescence tag. There were also rinse steps between and after these stages with either a blocking solution or PBS buffer (Phosphate-buffered saline with a pH of 7.4).

Preparation of MT Solutions at Low pH

The procedure for the testing of the stability of MTs in acidic conditions was performed as follows. MTs were exposed to a solution at a pH 4 for different times. A control was prepared by diluting the MT stock solution with PEMTAX (500:1 ratio of PEM80 buffer to taxol) at pH 6.9 and immediately adding a 2% glutaraldehyde solution (in PEM80) to the mixture. The overall dilution of the MTs in buffer and glutaraldehyde mixture was 1:50. Glutaraldehyde is a fixative (or setting agent) and cross-linking agent used to stabilize the MTs. The MTs were diluted 1:50 in a 0.02 M acetic acid to 0.02 M ascorbic acid solution with pH adjusted to 4.0 using KOH. This solution is the copper plating solution with the copper salt omitted. The purpose of this control was to determine if acetic acid and ascorbic acid had any adverse effects on the MTs. After 1, 3, and 5 minutes, the glutaraldehyde solution was introduced to the solution to arrest MT assembly and disassembly dynamics. This procedure was carried out for MTs and MTs stabilized with MAPs. The samples were deposited onto a commercially coated poly-L-lysine microscope slide and allowed to set for 30 minutes. The samples were treated with fluorescence immuno-labeling and followed by optical characterization with an epi-fluorescence microscope. The stability of MTs was measured in solution of acetic acid and ascorbic acid at pH 4. After 5 minutes, there was no significant change in the concentration or the dimension of the MTs. Since, copper deposition initiated after 90 seconds and formed a uniform film after approximately 4 minutes, the metallization of MTs in an acidic solution was deemed feasible.

Copper Electroless Plating Solutions

Electroless copper plating solutions were optimized by preliminary deposition experiments on platinum foil. The reduction chemistry for copper metallization was optimized to generate a thin, uniform film of copper at a physiological useful pH which could then be applied to microtubules. One useful copper plating solution identified was an aqueous solution (0.01 M copper sulfate, 0.02 M acetic acid, 0.02 M ascorbic acid solution at pH 4). This type of optimization can be employed to optimize conditions for metallization employing different reducible metal salts, different reducing agents and different complexants. This type of optimization can be employed to optimize conditions for metallization with metals other than copper, and particularly for metallization with gold.

The plating or metallization solution was prepared by mixing appropriate amounts of 0.1 M copper sulfate and 0.1 M acetic acid. The pH of the ascorbic acid solution was adjusted by addition of 1 M KOH so that the addition of ascorbic acid to the copper sulfate and acetic acid solution would yield a final pH of 4. KOH was added to the ascorbic acid rather than the copper sulfate solution to prevent the formation of copper oxide. Ascorbic acid was added to the plating solution last yielding a final concentration of 0.01 M copper sulfate, 0.02 M acetic acid and 0.02 M ascorbic acid at a pH of 4.

Metallization of MTs

The Cu plating solution was added to the MT stock solution in a ratio of 25:1. After time periods of 1, 2 and 4 minutes had elapsed, a 2% glutaraldehyde solution in PEM80 was added to the metalized MTs (a 50:1 dilution of the MTs). The glutaraldehyde solution was added to dilute the plating solution and stop metallization (under these conditions glutaraldehyde should not fix or cross-link MTs). To eliminating excess salts for viewing the MTs under FESEM, TEM, and AFM, the solution containing metalized MTs was dialyzed by injecting it into a Slide-A-Lyzer dialysis cassette (Pierce Biotechnology, Inc.) and submerged into a DI water bath which was more than 200 times the volume inside the cassette for at least 8 hours. Dialyzed metalized MTs were concentrated by microcentrifugation for 10 minutes at 13.2 rpm. MTs were collected and dried onto a carbon coated nickel grid (Ted Pella, Inc.). Samples were dried for at least 12 hours before imaging. This method can be used for optimizing the time of metallization needed for metallization of biological macromolecules and structures other than MTs. This method can also be used for optimizing the time of metallization needed employing variant metallization solutions (for other metallization components and for metallization with metals other than copper.

Images of metalized microtubules were analyzed with several characterization techniques including a Hitachi S4500 Scanning Electron Microscope and a Hitachi H8100 Transmission Electron Microscope. Analysis and presence of the copper film on the microtubules was confirmed using Thermo-Noran Digital Imaging/energy-dispersive spectroscopy (EDS) capabilities of the SEM and TEM.

The specific copper ion source in the Cu-plating chemistry herein was a copper sulfate solution. Different source of copper ion can be employed, e.g., copper nitrate, copper chloride, copper acetate etc. Several reducing agents were investigated: ascorbic acid and NADH. Ascorbic acid alone or in combination with NADH was shown to reduce copper ions to copper. Since ascorbic acid is sufficient in this electroless plating process, the use of NADH was discontinued due to its high cost. Additionally, many complexants and copper ion stabilizers were studied to alter the kinetics of reduction of copper and control copper particle size. Acetic acid was incorporated into the chemistry to complex copper. Copper ions complex with 1 to 3 molecules of acetic acid. For this reason, the molar concentration of acetic acid used in the metallization solution was 2 times greater than the concentration of the copper sulfate.

At pH higher (more basic) than 4.3, the formation of copper oxide (cuprite) precipitate was observed to be greater than metallic copper. Copper oxide formation will generally be higher at more basic pH values. Therefore, it was determined that the best pH for this 0.01 M copper sulfate to 0.02 M acetic acid to 0.02 M ascorbic acid metallization solution was a value of 4. Similar principles and routine experimentation can be employed to optimize the pH and temperature of metallization with other copper salts and other reducible metal salts.

Electroless Plating and Characterization of Metalized MTs

Figure 4:
FIG. 4 is a TEM micrograph of Cu-metalized MTs on carbon coated nickel grid (200 kV magnification). MTs were treated with a metallizing composition (0.01 copper sulfate, 0.02 acetic acid, 0.02 M ascorbic acid, pH 4.0) for 1 minute.
Figure 5:
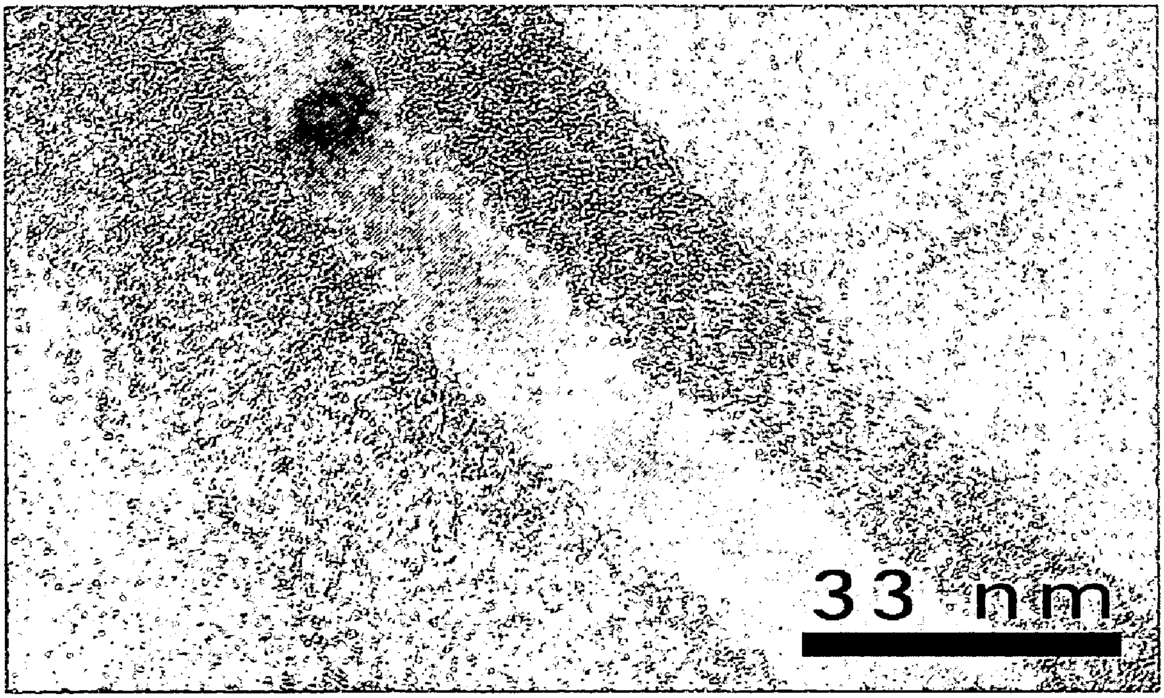
FIG. 5 is a high resolution TEM micrograph of a section of the Cu-metalized MTs of FIG. 4.

MTs metalized for 1 minute employing the copper metallization solution described above were observed by analysis of TEM micrographs collected employing standard techniques to have uniform diameters that ranged from 10 to 18 nm as shown in FIG. 4. At higher magnification, TEM micrographs showed dark regions of the metalized MT (FIG. 5). Analysis of these TEM micrographs indicates that at shorter times metallization with copper is occurring on the inside of the MT (see FIG. 1 for an illustration of the inner surface of the MT), rather than or on the outside of the MT followed by collapse of the metalized MT to give the small diameter wires. The high resolution images consistently show regions along the nanowire where continuous lattice fringes occupy the entire diameter of the wire. In FIG. 5 lattice fringes can be observed which indicate crystalline copper extends over the width of the entire diameter of the wire and extends more than 60 nm in length. If the small diameter metalized MT had be formed via collapse of the MT walls it would be expected that there would be more evidence in the TEM of voids or spaces between the two copper walls.

The structures of MTs metalized for 2 minutes were analyzed using SEM (not shown). The dimensions of the metalized MTs were found (by TEM) to have diameters ranging from 10-17 nm. The metalized MTS formed also exhibit uniform metal coating compared.

Figure 6:
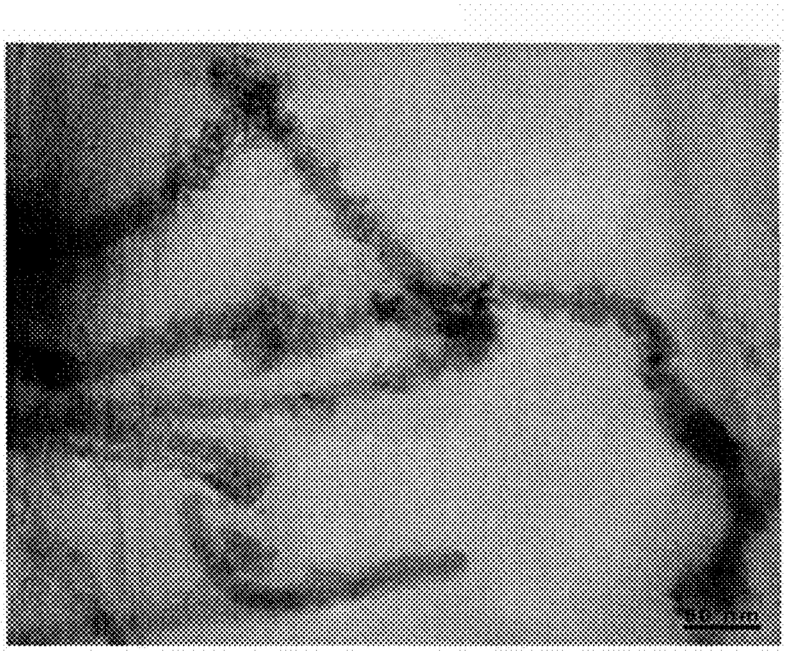
FIG. 6 is a TEM micrograph of metalized MTs for 4 minutes on carbon coated nickel grid (200 kV magnification). MTs were treated with a metallizing composition (0.01 copper sulfate, 0.02 acetic acid, 0.02 M ascorbic acid, pH 4.0) for 4 minute.

MTs metalized for 4 minutes were observed by analysis of TEM micrograph collected employing standard techniques to have non-uniform diameters that ranged from 13 to 32 nm. Along the length of one MT, the diameter varied as shown in FIG. 6. EDS was used to confirm that the composition of the coating on the MT was copper. This is supported by the fact that there were also lattice fringes along the microtubules indicating portions of crystalline material.

It is common for metallic ions to diffuse through the porous membrane of the MT and adsorb on the interior wall of the MT. The reduction of the copper ions at the interior wall could be a result of the oxidation of certain amino acids exposed on that wall or the oxidation of ascorbic acid. Once metal nuclei are formed, they can then catalyze metallization of the inside hollow tube of the MT. Histidine which functions as a ligand towards transition metals is known to have available binding sites on the inner surface of the MT and may be the substance responsible for the binding of copper ions. The presence of the dark copper particles in the TEM images of the MTs metalized for 1 minute is also of interest. There may be a periodicity of occurrence of copper particles which may correspond with a specific binding site. The contrast of these particles is very similar and indicates that their orientation is the same or very close to being the same. The distance between these two particles is about 150 nm. The spacing between an alpha and beta tubulin is known to be 8 nm, and a sequence of the MTs repeats itself after 3 or 5 helices are formed (three-start and five-start helices). It is unclear at this time what the relevance the periodicity of copper particles is.

Evidence for Copper Deposition on Inside of MT

The diameters of the copper wires produced by the metallization of MTs indicate that the inside walls of the MT is being metalized, simply because of the dimensions observed. From the TEM micrographs obtained from the samples of MTs metalized for 1 to 4 minutes, the diameters of the copper wires were measured and recorded. For each sample, the diameters of 5 different MTs were measured. The diameters were measured approximately every 150 nm along the length of the MT and included regions of large and small diameters. As mentioned before, there were large copper particles that were attached to the ends of some MTs. In this case, the MT diameter was measured up to the copper particle and usually had a large diameter value. It should be noted that no preconceived criterion was made in the TEM imaging of the metalized MTs or the measurement of the copper wire diameters.

The average diameters of the 5 nanowires produced from the metallization of MTs after 1 minute, ranged from 11.5 to 21.4 nm. The overall average of the 5 MTs was determined to be 15.2 nm with a standard deviation of 4.7. The same calculations for the nanowires produced after 2 minutes, were an overall average of 16.8 nm and a standard deviation of 3.0. In the data for metallization for 4 minutes, the overall average and the standard deviation were calculated to be 23.9 nm and 6.1, respectively. The latter average is less than the outside diameter of the uncoated MTs (25 nm), suggesting that the inside of the MTs is indeed metalized.

Figure 7:
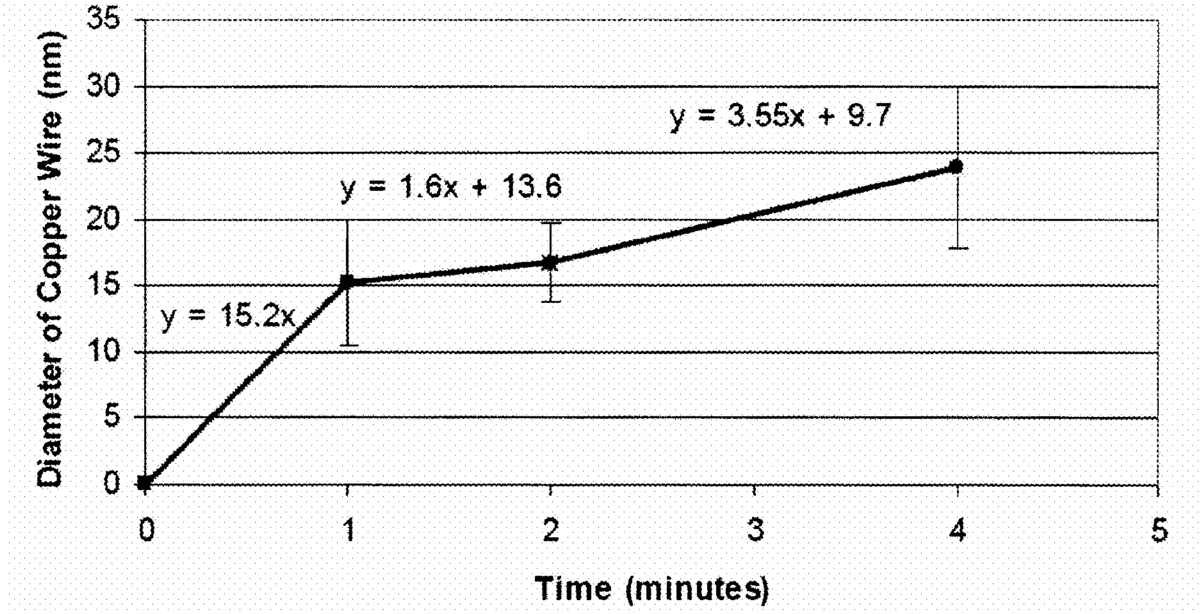
FIG. 7 is a graph illustrating the rate of copper metallization as a function of time based on the average diameter (nm) of copper wires formed.

The values obtained for the overall averages were plotted vs. their respective metallization times. The graph is shown in 7. The copper deposition rate after 1 minute was calculated to be 15.2 nm/min. This rate is similar to that observed for copper deposition on a gold electrode determined by QCM using the same metallization conditions as used for metallization of MTs. As seen in FIG. 7, the copper deposition rate drops drastically from 1 to 2 minutes and becomes steady from 2 to 4 minutes. The copper deposition rate decreases rapidly after 1 minute, when the diameter of the copper wire is approximately 15 nm, This suggests that copper deposition is slowed because the tubulin wall acts as an obstacle for further copper deposition.

In work by Kirsch et al., MTs were metalized with nickel. During the initial activation of MTs with $Pd^{2+}$ ions it was proposed that the amino acids cysteine, histidine and tryptophan were possible ligands for the Pd ions. Once the Pd ions were adsorbed onto the MT surface, cysteine was responsible for reducing the Pd ions to metallic Pd. Even though Pd ions were expected to penetrate the porous membrane of the MT, no metallization was observed in these experiments on the inner channel of the MT (the interior wall of the MT). This was believed to result because the cysteines were expected to only be active on the outer surface of the MT. The result was the metallization of only the outside of the MT. It was also postulated that the metallization of the outside of the MT was too fast to allow the Pd ions to penetrate the MT in the first place [R. Kirsch, M. Mertig, W. Pompe, R. Wahl, G. Sadowski, K. J. Böhm, and E. Unger, Thin Solid Films 1997, 305, 248.]

Three amino acid residues are of particular interest for binding to copper ions: histidine, cysteine and tryptophan. The location of these amino acids on the MT structure was considered. There are about 5 histidines/dimer on the inside surface of the MT. Histidine, particularly the nitrogen atom of the imidazole group in histidine, is known to have a high affinity for copper (II) ions. While copper also has a high affinity for the sulfhydryl group of cysteine residues, the occurrence of a free cysteine residue is rare. The expected higher surface density of histidine residues on the inner surface of the MT may be the reason for the preferred metallization from that surface. Based on the experimental results, a mechanism is proposed for the metallization of the inside of the MTs. First, the Cu (II) ions and copper-acetic acid complex diffuse through the porous wall of the MT. In the interior chamber of the MT, the copper ions and copper-acetate ions bind to the imidazole group of histidine residues and copper-acetate is converted to a copper-imidazole complex. Next, ascorbic acid penetrates the MT wall and reduces the copper ions to metallic copper nuclei. These copper nuclei catalyze further copper metallization on the inside of the MT.

When a Markush group or other grouping is used herein, all individual members of the group and all combinations and possible subcombinations of the group are intended to be individually included in the disclosure. Every formulation or combination of components described or exemplified herein can be used to practice the invention, unless otherwise stated. One of ordinary skill in the art will appreciate that methods, device elements, and materials other than those specifically exemplified can be employed in the practice of the invention without resort to undue experimentation. All art-known functional equivalents, of any such methods, device elements, and materials are intended to be included in this invention. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this invention. The invention illustratively described herein suitably may be practiced in the absence of any element or elements, limitation or limitations which is not specifically disclosed herein.

A number of specific groups have been described herein. It is intended that all combinations and subcombinations of the specific groups that have been described are individually included in this disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants may also be useful in diagnostic assays and in therapeutics. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

Although the description herein contains many specificities, these should not be construed as limiting the scope of the invention, but as merely providing illustrations of some of the embodiments of the invention. Each reference cited herein is hereby incorporated by reference in its entirety. However, if any inconsistency arises between a cited reference and the present disclosure, the present disclosure takes precedent. Some references provided herein are incorporated by reference to provide details concerning the state of the art prior to the filing of this application, other references may be cited to provide additional or alternative sources for materials, device elements, additional or alternative materials, additional or alternative methods of analysis or additional or alternative applications of the methods and materials of the invention.

The invention claimed is:

1. A method for metallizing a microtubule comprising the step of contacting the microtubule with a reducible metal salt in the presence of a reducing agent at a pH of 4 for a time sufficient to achieve a desired level of coating of the protein with the reduced metal on a surface of the microtubule, wherein the microtubule is not fixed or crosslinked prior to metallization.

2. The method of claim 1 wherein the reducible metal is copper.

3. The method of claim 1 where the reducible metal is gold or silver.

4. The method of claim 1 wherein the reducing agent is ascorbic acid or ascorbate.

5. The method of claim 1 wherein the microtubule is contacted with a metallization solution comprising the reducible metal salt and the reducing agent.

6. The method of claim 5 wherein the metallization solution further comprises a complexant.

7. The method of claim 6 wherein the complexant is acetic acid or acetate.

8. The method of claim 6 wherein the complexant is an organic acid or amine or a salt thereof, hydroxylamine or EDTA.

9. The method of claim 1 wherein the microtubule is attached at one or both ends to a solid substrate.

10. The method of claim 1, wherein the microtubule is not attached to a solid substrate.

11. The method of claim 1 wherein the reducible metal is Cu(II) and metallization is conducted at pH 4.0.

12. The method of claim 1 wherein the reducible metal is Cu(II), the reducing agent comprises ascorbic acid or ascorbate and metallization is conducted at pH 4.0.

13. The method of claim 1 wherein more than one contacting step is applied sequentially to obtain multiple layers of deposited metal.

14. The method of claim 1 wherein the microtubule is coated with two or more metals.

15. The method of claim 1 wherein the metal coating is continuous.

16. The method of claim 1 wherein the contacting step is conducted for 1-2 minutes.

17. The method of claim 1 wherein the contacting step is conducted in the presence of a stabilizing agent.

18. The method of claim 1 wherein the microtubule is attached to a substrate.

19. The method of claim 1 wherein the microtubule is metallized in the presence of taxol or a Microtubule Associated Protein.

20. The method of claim 1 wherein the outer surface of the microtubule is metallized.

21. The method of claim 1 wherein the inner surface of the microtubule is metallized.

22. The method of claim 1 wherein a nanowire is formed on metallization.

23. The method of claim 22 wherein the nanowire has a diameter ranging from 10-100 nm.

24. The method of claim 1 wherein the surface of the microtubule is not activated with a noble metal.

25. The method of claim 1 wherein the reducible metal is copper and the metallization is carried out for 1 to 5 minutes.

26. The method of claim 1 wherein the reducible metal is copper and the metallization is carried out for 1 to 2 minutes.

27. The method of claim 1 wherein the reducible metal is copper and uniform copper wire with a diameter of 15 nm is formed on metallization.

* * * * *